United States Patent
Brister et al.

(10) Patent No.: US 12,102,547 B2
(45) Date of Patent: *Oct. 1, 2024

(54) INTRAGASTRIC VOLUME-OCCUPYING DEVICE AND METHOD FOR FABRICATING SAME

(71) Applicant: Obalon Therapeutics, Inc., Carlsbad, CA (US)

(72) Inventors: Mark C. Brister, Encinitas, CA (US); Kaushik A. Patel, Poway, CA (US); Andrew P. Rasdal, San Diego, CA (US); Nelson Quintana, San Diego, CA (US); Neil R. Drake, San Diego, CA (US); Antonio C. Llevares, Chula Vista, CA (US); Dubravka Markovic, San Diego, CA (US); Amy D. L. VandenBerg, San Diego, CA (US)

(73) Assignee: RESHAPE LIFESCIENCES INC., Irvine, CA (US)

( * ) Notice: Subject to any disclaimer, the term of this patent is extended or adjusted under 35 U.S.C. 154(b) by 1104 days.

This patent is subject to a terminal disclaimer.

(21) Appl. No.: 16/865,242

(22) Filed: May 1, 2020

(65) Prior Publication Data
US 2020/0253767 A1    Aug. 13, 2020

Related U.S. Application Data

(63) Continuation of application No. 15/806,190, filed on Nov. 7, 2017, now Pat. No. 10,675,165, which is a
(Continued)

(51) Int. Cl.
*A61F 5/00* (2006.01)
*A61B 90/00* (2016.01)
(Continued)

(52) U.S. Cl.
CPC .............. *A61F 5/003* (2013.01); *A61B 90/39* (2016.02); *A61F 5/0036* (2013.01);
(Continued)

(58) Field of Classification Search
CPC ...... A61F 5/003; A61F 5/0036; A61F 5/0073; A61B 90/39; A61B 17/1204;
(Continued)

(56) References Cited

U.S. PATENT DOCUMENTS

| | | | |
|---|---|---|---|
| 2,183,900 A | 12/1939 | Voit et al. | |
| 3,786,813 A | 1/1974 | Michaels | |

(Continued)

FOREIGN PATENT DOCUMENTS

| | | |
|---|---|---|
| CN | 101249006 | 8/2008 |
| DE | 3540936 | 10/1986 |

(Continued)

OTHER PUBLICATIONS

Al Kahtani et al., Bio-Enteric Intragastric Balloon In Obese Patients: A Retrospective Analysis of King Faisal Specialist Hospital Experience, Obes Surg, Aug. 28, 2008, 8 pp.
(Continued)

*Primary Examiner* — Todd J Scherbel
(74) *Attorney, Agent, or Firm* — Knobbe, Martens, Olson & Bear LLP

(57) ABSTRACT

Intragastric volume-occupying devices and methods for treating obesity are provided. The devices, which are inflated by carbon dioxide, include an aluminum or silicon oxide barrier layer providing carbon dioxide retention and an alkylene vinyl alcohol polymer layer providing structural integrity in vivo.

11 Claims, 3 Drawing Sheets

Related U.S. Application Data continuation of application No. 14/724,708, filed on May 28, 2015, now Pat. No. 10,085,865, which is a continuation of application No. 12/580,044, filed on Oct. 15, 2009, now Pat. No. 9,072,583.

(60) Provisional application No. 61/105,932, filed on Oct. 16, 2008.

(51) Int. Cl.
| | |
|---|---|
| *A61L 31/08* | (2006.01) |
| *A61L 31/10* | (2006.01) |
| *A61M 25/10* | (2013.01) |
| *A61M 31/00* | (2006.01) |
| *A61B 17/12* | (2006.01) |

(52) U.S. Cl.
CPC .......... *A61F 5/0073* (2013.01); *A61F 5/0083* (2013.01); *A61L 31/088* (2013.01); *A61L 31/10* (2013.01); *A61M 25/10185* (2013.11); *A61M 25/1029* (2013.01); *A61M 31/002* (2013.01); *A61B 17/1204* (2013.01); *A61B 17/12099* (2013.01); *A61B 2090/3966* (2016.02); *A61L 2400/16* (2013.01); *A61L 2420/02* (2013.01); *A61L 2420/08* (2013.01); *A61M 25/1027* (2013.01); *A61M 2025/1031* (2013.01); *A61M 2025/105* (2013.01); *Y10T 156/1051* (2015.01)

(58) Field of Classification Search
CPC ..... A61B 17/12099; A61B 2090/3966; A61M 25/10185; A61M 25/1029; A61M 2025/105; A61L 31/10
See application file for complete search history.

(56) References Cited

U.S. PATENT DOCUMENTS

| | | | |
|---|---|---|---|
| 3,788,322 A | 1/1974 | Michaels | |
| 3,797,492 A | 3/1974 | Place | |
| 4,133,315 A | 1/1979 | Berman et al. | |
| 4,234,454 A | 11/1980 | Strope | |
| 4,236,521 A | 12/1980 | Lauterjung | |
| 4,246,893 A | 1/1981 | Berson | |
| 4,340,626 A | 7/1982 | Rudy | |
| 4,416,267 A | 11/1983 | Garren et al. | |
| 4,485,805 A | 12/1984 | Foster, Jr. | |
| 4,489,440 A | 12/1984 | Chaoui | |
| 4,517,979 A | 5/1985 | Pecenka | |
| 4,545,367 A | 10/1985 | Tucci | |
| 4,560,392 A | 12/1985 | Basevi | |
| 4,607,618 A | 8/1986 | Angelchik | |
| 4,694,827 A | 9/1987 | Weiner et al. | |
| 4,718,639 A | 1/1988 | Sherwood et al. | |
| 4,723,547 A | 2/1988 | Kullas et al. | |
| 4,739,758 A | 4/1988 | Lai et al. | |
| 4,812,315 A | 3/1989 | Tarabishi | |
| 4,813,934 A | 3/1989 | Engelson et al. | |
| 4,857,029 A | 8/1989 | Dierick et al. | |
| 4,899,747 A | 2/1990 | Garren et al. | |
| 4,917,885 A | 4/1990 | Chiba et al. | |
| 4,925,446 A | 5/1990 | Garay et al. | |
| 4,929,214 A | 5/1990 | Liebermann | |
| 5,049,106 A | 9/1991 | Kim et al. | |
| 5,084,061 A | 1/1992 | Gau et al. | |
| 5,129,915 A | 7/1992 | Cantenys et al. | |
| 5,234,454 A | 8/1993 | Bangs | |
| 5,259,399 A | 11/1993 | Brown | |
| 5,270,086 A | 12/1993 | Hamlin | |
| 5,308,326 A | 5/1994 | Zimmon | |
| 5,431,917 A | 7/1995 | Yamamoto et al. | |
| 5,674,239 A | 10/1997 | Zadini | |
| 5,713,141 A | 2/1998 | Mitchell et al. | |
| 5,728,119 A | 3/1998 | Smith et al. | |
| 5,817,099 A | 10/1998 | Skolik et al. | |
| 5,852,889 A | 12/1998 | Rinaldi | |
| 5,868,141 A | 2/1999 | Ellias | |
| 5,897,205 A | 4/1999 | Sinsteden | |
| 5,910,128 A | 6/1999 | Quinn | |
| 5,938,669 A | 8/1999 | Klaiber | |
| 6,427,089 B1 | 7/2002 | Knowlton | |
| 6,454,785 B2 | 9/2002 | De Hoyos Garza | |
| 6,579,301 B1 | 6/2003 | Bales et al. | |
| 6,627,206 B2 | 9/2003 | Lloyd | |
| 6,682,473 B1 | 1/2004 | Matsuura et al. | |
| 6,689,141 B2 | 2/2004 | Ferrera | |
| 6,733,512 B2 | 5/2004 | McGhan et al. | |
| 6,981,980 B2 | 1/2006 | Sampson et al. | |
| 6,988,983 B2 | 1/2006 | Connors et al. | |
| 7,101,396 B2 | 9/2006 | Artof et al. | |
| 7,112,186 B2 | 9/2006 | Shah | |
| 7,192,397 B2 | 3/2007 | Lewkowicz et al. | |
| 7,674,396 B2 | 3/2010 | Sterling | |
| 7,682,306 B2 | 3/2010 | Shah | |
| 7,699,863 B2 | 4/2010 | Marco et al. | |
| 7,753,949 B2 | 7/2010 | Lamphere et al. | |
| 7,785,291 B2 | 8/2010 | Marco | |
| 7,854,745 B2 | 12/2010 | Brister et al. | |
| 7,879,355 B2 | 2/2011 | Sterling | |
| 7,972,378 B2 | 7/2011 | Tabor et al. | |
| 8,066,780 B2 | 11/2011 | Chen | |
| 8,162,969 B2 | 4/2012 | Brister et al. | |
| 8,202,291 B1 | 6/2012 | Brister et al. | |
| 8,282,666 B2 | 10/2012 | Birk | |
| 8,287,562 B2 | 10/2012 | Kasic et al. | |
| 8,292,911 B2 | 10/2012 | Brister | |
| 8,562,589 B2 | 10/2013 | Imran | |
| 8,647,358 B2 | 2/2014 | Brister et al. | |
| 8,721,620 B2 | 5/2014 | Imran | |
| 8,734,429 B2 | 5/2014 | Imran et al. | |
| 8,740,927 B2 | 6/2014 | Brister et al. | |
| 8,764,733 B2 | 7/2014 | Imran | |
| 8,809,269 B2 | 8/2014 | Imran | |
| 8,809,271 B2 | 8/2014 | Imran | |
| 8,845,674 B2 | 9/2014 | Brister et al. | |
| 8,870,966 B2 | 10/2014 | Schwab et al. | |
| 8,992,561 B2 | 3/2015 | Brister et al. | |
| 9,011,477 B2 | 4/2015 | Brister et al. | |
| 9,072,583 B2 | 7/2015 | Brister et al. | |
| 9,173,758 B2 | 11/2015 | Brister et al. | |
| 9,351,862 B2 | 5/2016 | Brister et al. | |
| 9,468,550 B2 | 10/2016 | Brister et al. | |
| 9,539,132 B2 | 1/2017 | Brister et al. | |
| 9,662,239 B2 | 5/2017 | Brister et al. | |
| 9,827,128 B2 | 11/2017 | Brister et al. | |
| 10,085,865 B2 * | 10/2018 | Brister | ................ A61B 90/39 |
| 10,327,936 B2 | 6/2019 | Brister et al. | |
| 10,463,520 B2 | 11/2019 | Brister et al. | |
| 10,537,453 B2 | 1/2020 | Brister et al. | |
| 10,610,396 B2 | 4/2020 | Brister et al. | |
| 10,675,165 B2 | 6/2020 | Brister et al. | |
| 10,874,537 B2 * | 12/2020 | Brister | ................ A61M 31/002 |
| 2003/0021822 A1 | 1/2003 | Lloyd | |
| 2003/0171768 A1 | 9/2003 | McGhan | |
| 2004/0044351 A1 | 3/2004 | Searle | |
| 2004/0044357 A1 | 3/2004 | Gannoe | |
| 2004/0102677 A1 | 5/2004 | Frering | |
| 2005/0118370 A1 | 6/2005 | Varma et al. | |
| 2005/0222329 A1 | 10/2005 | Shah et al. | |
| 2005/0266109 A1 | 12/2005 | Chin et al. | |
| 2005/0267405 A1 | 12/2005 | Shah | |
| 2005/0267595 A1 | 12/2005 | Chen et al. | |
| 2006/0058829 A1 | 3/2006 | Sampson et al. | |
| 2006/0127439 A1 * | 6/2006 | Mattes | ................ A61L 29/043 |
| | | | 623/1.11 |
| 2006/0224145 A1 | 10/2006 | Gillis et al. | |
| 2007/0078476 A1 | 4/2007 | Hull et al. | |
| 2007/0100208 A1 | 5/2007 | Lewkowicz et al. | |
| 2007/0100369 A1 | 5/2007 | Cragg et al. | |
| 2007/0104754 A1 | 5/2007 | Sterling et al. | |
| 2007/0104755 A1 | 5/2007 | Sterling et al. | |
| 2007/0118168 A1 | 5/2007 | Lointier | |

(56) References Cited

U.S. PATENT DOCUMENTS

| | | |
|---|---|---|
| 2007/0149994 A1 | 6/2007 | Sosnowski et al. |
| 2007/0156248 A1 | 7/2007 | Marco et al. |
| 2007/0173881 A1 | 7/2007 | Birk et al. |
| 2007/0207199 A1 | 9/2007 | Sogin et al. |
| 2007/0208373 A1* | 9/2007 | Zaver .................. A61F 2/0105 606/200 |
| 2007/0212559 A1 | 9/2007 | Shah |
| 2007/0250020 A1 | 10/2007 | Kim |
| 2007/0250087 A1 | 10/2007 | Makower |
| 2007/0250101 A1 | 10/2007 | Horn et al. |
| 2007/0288033 A1 | 12/2007 | Murature et al. |
| 2008/0051866 A1 | 2/2008 | Chen et al. |
| 2008/0172079 A1 | 7/2008 | Birk |
| 2008/0215003 A1 | 9/2008 | Kornerup |
| 2008/0243166 A1 | 10/2008 | Paganon |
| 2008/0255601 A1 | 10/2008 | Birk |
| 2008/0306506 A1 | 12/2008 | Leatherman et al. |
| 2009/0082644 A1 | 3/2009 | Li |
| 2009/0105687 A1 | 4/2009 | Deckman |
| 2009/0118756 A1 | 5/2009 | Valencon et al. |
| 2009/0182368 A1 | 7/2009 | Lunsford et al. |
| 2009/0182424 A1 | 7/2009 | Marco et al. |
| 2009/0192535 A1 | 7/2009 | Kasic, II et al. |
| 2009/0222065 A1 | 9/2009 | Dlugos et al. |
| 2009/0259246 A1 | 10/2009 | Eskaros et al. |
| 2010/0063530 A1 | 3/2010 | Valencon |
| 2010/0100115 A1 | 4/2010 | Soetermans et al. |
| 2010/0168782 A1 | 7/2010 | Hancock |
| 2010/0198249 A1 | 8/2010 | Sabliere |
| 2010/0222802 A1 | 9/2010 | Gillespie et al. |
| 2011/0202127 A1 | 8/2011 | Mauch et al. |
| 2011/0295300 A1 | 12/2011 | Verd et al. |
| 2012/0010590 A1 | 1/2012 | Imran |
| 2012/0269365 A1 | 1/2012 | Ochial et al. |
| 2012/0191124 A1 | 7/2012 | Brister |
| 2012/0265234 A1 | 10/2012 | Brister |
| 2012/0296365 A1 | 11/2012 | Nguyen |
| 2013/0165859 A1 | 6/2013 | Imran |
| 2013/0226219 A1 | 8/2013 | Brister et al. |
| 2013/0267983 A1 | 10/2013 | Pavlovic et al. |
| 2014/0066968 A1 | 3/2014 | Pavlovic et al. |
| 2014/0221912 A1 | 8/2014 | Imran |
| 2014/0221927 A1 | 8/2014 | Imran et al. |
| 2015/0374525 A1 | 12/2015 | Brister et al. |
| 2016/0193064 A1 | 7/2016 | Brister et al. |
| 2017/0027728 A1 | 2/2017 | Brister et al. |
| 2018/0221633 A1 | 8/2018 | Brister et al. |
| 2019/0269541 A1 | 9/2019 | Brister |
| 2020/0100925 A1 | 4/2020 | Brister |
| 2020/0179147 A1 | 6/2020 | Brister |

FOREIGN PATENT DOCUMENTS

| | | |
|---|---|---|
| EP | 0 103 481 | 3/1984 |
| EP | 0 213 748 | 3/1987 |
| EP | 0 246 999 | 11/1987 |
| WO | WO 87/00034 | 1/1987 |
| WO | WO 99/25418 | 5/1999 |
| WO | WO 01/68007 | 9/2001 |
| WO | WO 02/16001 | 2/2002 |
| WO | WO 02/40081 | 5/2002 |
| WO | WO 02/091961 | 11/2002 |
| WO | WO 03/055420 | 7/2003 |
| WO | WO 04/084763 | 10/2004 |
| WO | 05/094257 | 10/2005 |
| WO | WO 06/020929 | 2/2006 |
| WO | WO 07/136735 | 11/2007 |
| WO | WO 09/055386 | 4/2009 |
| WO | WO 09/059802 | 5/2009 |
| WO | WO 09/059803 | 5/2009 |
| WO | WO 09/086119 | 7/2009 |

OTHER PUBLICATIONS

Al-Momen et al., Intragastric Balloon for Obesity: A Retrospective Evaluation of Tolerance and Efficacy, Obes Surg, 2005,15(1):101-105.

Benjamin et al., Double-Blind Controlled Trial of the Garren-Edwards Gastric Bubble: An Adjunctive Treatment for Exogenous Obesity, Gastroenterology, Sep. 1988, 95(3):581-588.

Carvalho et al., An Improved Intragastric Balloon Procedure Using a New Balloon: Preliminary Analysis of Safety and Efficacy, Obes Surg, 2008, 6 pp.

Coskun et al., Bioenterics Intragastric Balloon: Clinical Outcomes of the First 100 Patients—A Turkish Experience, Obes Surg, Sep. 2008, 18(9):1154-6. published online Jun. 3, 2008.

Dastis et al., Intragastric Balloon for Weight Loss: Results in 100 Individuals Followed for at Least 2.5 Years, Endoscopy, Jul. 2009, 41(7):575-580.

De Waele et al., Endoscopic vol. Adjustment of Intragastric Balloons for Intolerance, Obes Surg, Apr. 2001. 11(2):223-224.

Doldi et al., Treatment of Morbid Obesity With Intragastric Balloon in Association With Diet, Obes Surg, 2002, 12(4):583-587.

Dumonceau, Evidence-Based Review of the Bioenterics Intragastric Balloon for Weight Loss, Obes Surg. Dec. 2008, 18(12): 1611-1617.

Durrans et al., Comparison of Weight Loss With Short Term Dietary and Intragastric Balloon Treatment, Gut 1989, 30:565-568.

Eckhauser et al., Hydrostatic Balloon Dilation for Stomal Stenosis after Gastric Partitioning, Surgical Gastroenterology, 3(1):43-50, 1984.

Evans et al., Intragastric Balloon in the Treatment of Patients With Morbid Obesity, British Journal of Surgery, 2001, 88:1245-1248.

Fernandes et al., Intragastric Balloon for Obesity (Review), Cochrane Review, Jan. 24, 2007, Issue 1.

Forestieri et al., Hellosphere Bag in the Treatment of Severe Obesity: Preliminary Experience, Obes Surg, May 2006, 16(5):635-637.

Gaggiotti et al., Adjustable Totally Implanted Intragastric Prosthesis (ATIIP). Endogast for Treatment of Morbid Obesity: One Year Follow-Up of a Multicenter Prospective Clinical Survey, Obesity Surgery, 2007, 17, 949-956.

Geliebter et al., Gastric balloon to treat obesity: a double-blind study in nondieting subjects, The American Journal of Clinical Nutrition, 1990, 51:584-588.

Genco et al., Bioenterics Intragastric Balloon (BIB): A Short-Term, Double-Blind, Randomized, Controlled, Crossover Study on Weight Reduction in Morbidly Obese Patients, International Journal of Obesity (Lond), Jan. 2006, 30(1):129-33, published online Sep. 27, 2005.

Genco et al., Bioenterics Intragastric Balloon: The Italian Experience With 2,515 Patients, Obes Surg, 2005, 15(8):1161-1164.

Genco et al., Intragastric Balloon or Diet Alone? A Retrospective Evaluation, Obes Surg, Aug. 2008, 18(8):989-92. published online May 16, 2008.

Genco et al., Laparoscopic Sleeve Gastrectomy Versus Intragastric Balloon: A Case-Control Study, Surg Endosc. Springer Science & Business Media, published online Jan. 24, 2009.

Gottig et al., Analysis of Safety and Efficacy of Intragastric Balloon in Extremely Obese Patients, Obes Surg, Jun. 2009, 19(6):677-683. published online Mar. 17, 2009.

Imaz et al., Safety and Effectiveness of the Intragastric Balloon for Obesity. A Meta-Analysis, Obes Surg, Jul. 2008,18(7):841-846, published online May 6, 2008.

Langer, R., Drug delivery and targeting, Nature, Suuplement to, Apr. 1998, 392(6679):5-10.

Malik, Endoluminal and Transluminal Surgery: Current Status and Future Possibilities, Surgical Endoscopy, 2006, 20(8):1179-1192.

Martin et al., Safety of the Ullorex Oral Intragastric Balloon for the Treatment of Obesity, Journal of Diabetic Science and Technology, Jul. 2007, 1(4):574-581.

(56) References Cited

OTHER PUBLICATIONS

Mathus-Vliegen et al., Intragastric Ballon in the Treatment of Super-morbid Obesity—Double-Blind, Sham-Controlled, Crossover Evaluation of 500-Milliliter Balloon, Gastroenterology, Aug. 1990, 99(2):362-369.
Melissas et al., The Intragastric Balloon—Smoothing the Path to Bariatric Surgery, Obes Surg, 2006, 16:897-902.
Mion et al., Tolerance and Efficacy of an Air-Filled Balloon in Non-Morbidly Obese Patients: Results of a Prospective Multicenter Study, Obes Surg, Jul. 2007, 17(7):764-769.
Nieben et al., Ingtragastric Balloon as an Artificial Bezoar for Treatment of Obesity, The Lancet, Jan. 1982, 1(8265): 198-199.
Ramhamadany et al, Effect of the Gastric Balloon Versus Sham Procedure on Weight Loss in Obese Subjects, Gut, 1989, 30:1054-1057.
Rodriguez-Hermosa et al., Gastric Necrosis: A Possible Complication of the Use of the Intragastric Balloon in a Patient Previously Submitted to Nissen Fundoplication, Obes Surg, 19:1456-1459, published online Jun. 9, 2009.
Roman et al., Intragastric Balloon for "Non-Morbid" Obesity: A Retrospective Evaluation of Tolerance and Efficacy, Obes Surg, Apr. 2004, 14(4):539-544.
Sallet et. al. Brazilian Multicenter Study of the Intragastric Balloon, Obesity Surgery, Aug. 2004, 14(7):991-998.
Totte et al., Weight Reduction by Means of Intragastric Device: Experience With the Bioenterics Intragastric Balloon, Obes Surg, Aug. 2001 11(4):519-523.
Trande et al., Efficacy, Tolerance and Safety of New Intragastric Air-Filled Balloon (Heliosphere BAG) for Obesity: The Experience of 17 Cases, Obes Surg, Dec. 10, 2008.
Vansonnenberg et al., Percutaneous Gastrostomy: Use of Intragastric Ballon Support, Radiology, Aug. 1984, 152(2):531-532.
Wahlen et al., The Bioenterics Intragastric Balloon (BIB): How to Use It, Obes Surg, 2001, 11(4):524- 527.
DuPont, Newest Online Modeling Tool Simplifies Tie Layer Selection, product brochure, http://www2.dupont.com/Packaging_Resins/en_US/whats_new/article20120618_tie resin_tool.html, Jun. 18, 2012.
Dupont™ Bynel® resins, product brochure, http://www2.dupont.com/Bynel/en_US/—Copyright© 2012.
Lyondellbasell, Selecting a Tie-Layer Adhesive, product brochure, http://www.lyondellbasell.com/Products/ByCategory/polymers/type/Polyethylene/SpecialtyPolyethylene/TieLayerResins/Selecting_a_Tie_layer_Adhesive.htm—2012.
Lyondellbasell, Tie-Layer Resins, product brochure, http://www.lyondellbasell.com/Products/ByCategory/polymers/process/TieLayerResins/—2012.
Mitsui Chemicals America, Inc., ADMER™ Adhesive Resin, product brochure, http://www.mitsuichemicals.com/adm.htm, Copyright 1999-2012.
Westlake Chemical, Tie Layer, product brochure, http://www.westlake.com/fw/main/Tie-Layer-170.html—2012.
European Search Report dated Jun. 22, 2010 for EP App. No. 10004281.1 filed Mar. 17, 2004.
European Search Report dated Sep. 14, 2009 for EP App. No. 05786479 filed Aug. 15, 2005.
International Preliminary Report on Patentability dated Dec. 1, 2005 for PCT/US2004/008178 file Mar. 17, 2004.
International Preliminary Report on Patentability dated Jan. 13, 2009 for PCT/US2008/028850 filed Aug. 15, 2005.
International Search Report and Written Opinion dated Oct. 15, 2004 for PCT/US2004/08178 filed Mar. 17, 2004.
International Search Report dated Jul. 8, 2010 for PCT/US2009/060881 filed Oct. 15, 2009.
International Search Report dated Jun. 25, 2008 for PCT/US2005/28850 filed Aug. 15, 2005.
International Search Report issued in corresponding PCT Application No. PCT/US2009/060874, mailed May 26, 2010.

* cited by examiner

INTRAGASTRIC VOLUME-OCCUPYING DEVICE AND METHOD FOR FABRICATING SAME

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 15/806,190, filed Nov. 7, 2017, which is a continuation of U.S. application Ser. No. 14/724,708, filed May 28, 2015, now U.S. Pat. No. 10,085,865, which is a continuation of U.S. application Ser. No. 12/580,044, filed Oct. 15, 2009, now U.S. Pat. No. 9,072,583, which claims the benefit of U.S. Provisional Application No. 61/105,932, filed Oct. 16, 2008. Each of the aforementioned applications is incorporated by reference herein in its entirety, and each is hereby expressly made a part of this specification.

FIELD OF THE INVENTION

Intragastric volume-occupying devices and methods for treating obesity are provided. The devices, which are inflated by carbon dioxide, include an aluminum or silicon oxide barrier layer providing carbon dioxide retention and an alkylene vinyl alcohol polymer layer providing structural integrity in vivo.

BACKGROUND OF THE INVENTION

Obesity is a major health problem in developed countries. Obesity is associated with a greater risk of developing high blood pressure, diabetes and many other serious health problems. In the United States, the complications of overweight and obesity are estimated to affect nearly one in three American adults. Except for rare pathological conditions, weight gain is directly correlated to overeating.

Noninvasive methods for reducing weight include increasing metabolic activity to burn calories and/or reducing caloric intake, either by modifying behavior or with pharmacological intervention to reduce the desire to eat. Other methods include surgery to reduce the stomach's volume, banding to limit the size of the stoma, and intragastric devices that reduce the desire to eat by occupying space in the stomach.

Intragastric volume-occupying devices provide the patient a feeling of satiety after having eaten only small amounts of food. Thus, the caloric intake is diminished while the subject is satisfied with a feeling of fullness.

SUMMARY OF THE INVENTION

Currently available intragastric volume-occupying devices have many shortcomings. These can include the necessity of complex and/or uncomfortable procedures to insert and/or remove the device; insufficient control of timing of inflation and/or deflation; insufficient control of the process of inflation and/or deflation; and inability to maintain a proper level of inflation in vivo over a desired time period. The intragastric volume-occupying devices of the preferred embodiments can overcome one of more of these shortcomings. Methods for manufacturing, deploying, inflating, tracking, deflating and retrieving of the intragastric volume-occupying devices of the preferred embodiments are also provided, as are methods for treating obesity using the volume-occupying devices of the preferred embodiments.

Invasive procedures for deploying and/or recovering the intragastric volume-occupying devices of the preferred embodiments are not necessary; instead the devices are simply swallowed by a patient. Once in the stomach of the patient, the device increases in volume. After a predetermined time period has passed, or upon demand, the device decreases in volume and passes through the remainder of the patient's digestive tract. Inflation is achieved through a chemical reaction between reactive agents producing an inflation gas, e.g., carbon dioxide. The intragastric volume-occupying devices of the preferred embodiments comprise a composite film enclosing a space susceptible to volume expansion upon generation of the inflation gas. The composite film employed in the wall(s) of the intragastric volume-occupying devices of the preferred embodiments include silicon oxides (SiOx; silica) or aluminum oxides (AlOx; alumina) as a carbon dioxide-retaining component. The composite film also includes alkylene vinyl alcohol polymers which provide improved structural integrity for the wall(s) of the intragastric volume-occupying devices.

In a first aspect, an intragastric balloon system is provided comprising a composite wall structure configured to maintain a $CO_2$ leak rate of less than or equal to 40 $cc/m^2/day$ at 37° C., wherein the composite wall structure comprises: a supporting film structure having a Young's Modulus of 500 Mpa or greater; a first $CO_2$ barrier layer configured such that its $CO_2$ barrier properties are not substantially affected by exposure to humidity levels within the gastric environment or within a central lumen of the balloon; and a second $CO_2$ barrier layer configured such that its $CO_2$ barrier properties are not substantially affected by mechanical forces during processing, compacting, or application of external gastric pressures.

In an embodiment of the first aspect, the first $CO_2$ barrier layer comprises a silicon dioxide layer having a thickness of from about 100 Å to about 800 Å.

In an embodiment of the first aspect, the second $CO_2$ barrier layer comprises an ethylene vinyl alcohol layer having a thickness of at least about 2 microns.

In an embodiment of the first aspect, the first $CO_2$ barrier layer comprises a silicon dioxide layer having a thickness of from about 100 Å to about 800 Å and the second $CO_2$ barrier layer comprises an ethylene vinyl alcohol layer having a thickness of at least about 2 microns.

In an embodiment of the first aspect, the supporting film structure comprises a polyethylene terephthalate layer.

In an embodiment of the first aspect, the silicon dioxide layer is provided as a coating on one side of the polyethylene terephthalate layer.

In an embodiment of the first aspect, the ethylene vinyl alcohol layer is situated between two polyethylene layers, wherein the ethylene vinyl alcohol layer and the two polyethylene layers are bonded together with tie layers, and wherein the silicon dioxide layer is adhesively bonded to one of the polyethylene layers.

In an embodiment of the first aspect, the ethylene vinyl alcohol layer is extruded.

In an embodiment of the first aspect, the ethylene vinyl alcohol layer is co-extruded with one or more layers of polyethylene.

In an embodiment of the first aspect, the ethylene vinyl alcohol layer is sandwiched between two polyethylene layers.

In an embodiment of the first aspect, the intragastric balloon system is configured to be swallowable.

In an embodiment of the first aspect, the intragastric balloon system is configured to be self-inflating.

In an embodiment of the first aspect, the intragastric balloon system is configured to be swallowable and self-inflating.

In an embodiment of the first aspect, the intragastric balloon system further comprises a self-sealing valve system attached to the composite wall of the balloon in a central lumen of the balloon by an adhesive with a shear force greater than about 40 N, the self-sealing valve system comprising a septum, a retaining structure, and a continuous ring, wherein the septum has a durometer that is less than a durometer of the retaining structure, wherein the continuous ring is configured to exert a compressive force on the septum, wherein the balloon has a weight of less than about 15 g, wherein the balloon is configured to have a shape upon full inflation selected from the group consisting of ellipsoid, spheroid, and oblate spheroid, and wherein the balloon is configured to have a volume of from about 90 cm$^3$ to about 350 cm$^3$ upon full inflation.

In an embodiment of the first aspect, the intragastric balloon system further comprises an inner container within the central lumen of the balloon, the inner container containing from about 0.28 grams to about 4 grams of an inflation agent, wherein up to about 80 wt. % of a total amount of the inflation agent is powdered citric acid, with a remainder of the inflation agent comprising powdered sodium bicarbonate.

In a second aspect, a method is provided for fabricating a composite wall for use in an intragastric balloon system, comprising: providing a polyethylene terephthalate layer coated with a silicon dioxide layer having a thickness of from about 100 Å to about 800 Å; providing a trilayer system comprising ethylene vinyl alcohol layer sandwiched between polyethylene layers; and adhesively bonding the silicon dioxide layer to one of the polyethylene layers, whereby a composite wall structure configured to maintain a $CO_2$ leak rate of less than or equal to 40 cc/m$^2$/day at 37° C. is obtained.

In an embodiment of the second aspect, a thickness of the composite wall structure is 2.5 mil or less.

In an embodiment of the second aspect, the ethylene vinyl alcohol layer is bonded to the polyethylene layers via tie layers.

In an embodiment of the second aspect, the method further comprises forming the composite wall into two components, each component having a same shape selected from the group consisting of elliptical, circular, and oval, wherein one of the components further comprises a hole having a smallest dimension of at least about 0.6 cm, and a largest dimension of no more than about 3.8 cm; bonding the components together to form a wall of a balloon; inverting the wall of the balloon through the hole; and applying a patch of a material to seal the hole, whereby a balloon having a smooth outer surface is obtained, wherein the balloon is configured to have a volume of from about 90 cm$^3$ to about 350 cm$^3$ upon full inflation.

In an embodiment of the second aspect, the method further comprises, before the step of bonding, adhering a self-sealing valve system to one of the components by an adhesive with a shear force greater than about 40 N, the self-sealing valve system comprising a septum, a retaining structure, and a continuous ring, wherein the septum has a durometer that is less than a durometer of the retaining structure, wherein the continuous ring is configured to exert a compressive force on the septum.

In an embodiment of the second aspect, the method further comprises, after the step of inverting and before the step of applying a patch, a step of placing an inner container within the inverted balloon, the inner container containing from about 0.28 grams to about 4 grams of an inflation agent, wherein up to about 80 wt. % of a total amount of the inflation agent is powdered citric acid, with a remainder of the inflation agent comprising powdered sodium bicarbonate, wherein the balloon has a weight of less than about 15 g.

BRIEF DESCRIPTION OF THE DRAWINGS

FIG. 2A depicts a silicone head 441 with radioopacity ring 442, trimmed 30 D silicone septum 443, Nylon 6 inoculation spacer 444, folded balloon 445, inner container 446, and outer container 447 as constituents of the system in unassembled form. FIG. 2B depicts a fully assembled outer container 447 including vent hole 448 aligned with septum 449 for puncture to inject liquid activation agent.

DETAILED DESCRIPTION OF THE PREFERRED EMBODIMENT

Figure 1:
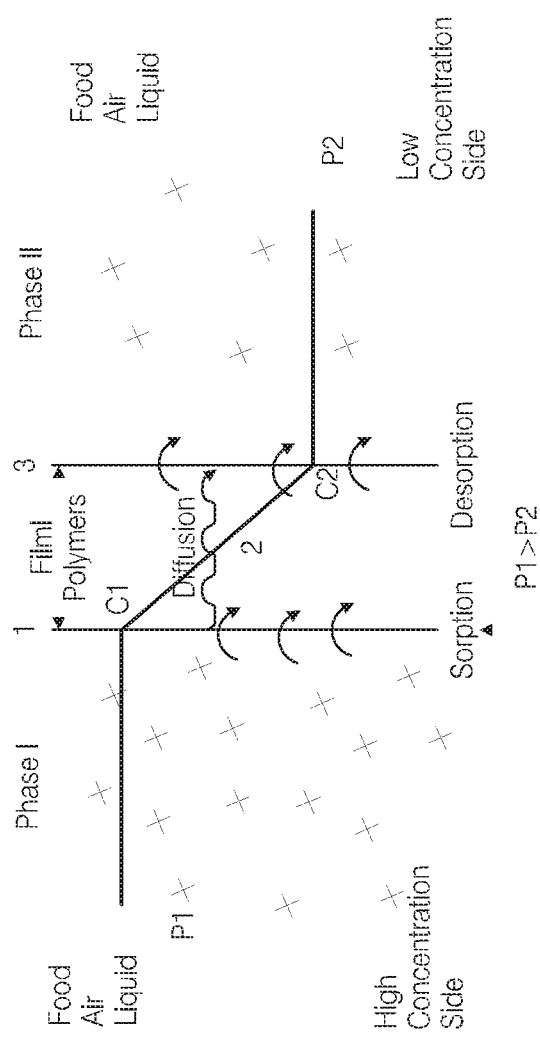
FIG. 1 is a diagram depicting the process of diffusion of, e.g., a gas, through a film.

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

An orally ingestible intragastric volume-occupying device that is able to traverse the alimentary canal is provided.

In certain preferred embodiments, a system including the device can include a volume-occupying subcomponent, an inflation subcomponent, a deflation subcomponent, and a delivery subcomponent. A tracking subcomponent and/or a drug delivery subcomponent can also optionally be employed.

The term "degradable" as used herein is a broad term, and is to be given its ordinary and customary meaning to a person of ordinary skill in the art (and is not to be limited to a special or customized meaning), and refers without limitation to a process by which structural integrity of the balloon is compromised (e.g., by chemical, mechanical, or other means (e.g., light, radiation, heat, etc.) such that deflation occurs. The degradation process can include erosion, dissolution, separation, digestion, disintegration, delamination, comminution, and other such processes.

The term "swallowable" as used herein is a broad term, and is to be given its ordinary and customary meaning to a person of ordinary skill in the art (and is not to be limited to a special or customized meaning), and refers without limitation to ingestion of a balloon by a patient such that the outer capsule and its constituents are delivered to the stomach via normal peristalsis movement. While the systems of preferred embodiments are swallowable, they are also configured by ingestion by methods other than swallowing. The swallowability of the system is derived, at least in part, by the outer container size, which is sufficient to contain the inner container and its constituents, an amount of activation agent injected prior to administration, the balloon size, and the balloon material thickness. The system is preferably of a size less than the average normal esophagus diameter.

Inflation Subcomponents

The intragastric volume-occupying devices of preferred embodiments are intended for ingestion by a patient and deployment without the need to resort to invasive methods. It is therefore desirable that the device be operable to conform to a compact delivery state which can be swallowed by a patient with minimal discomfort. Typically, in the delivery state, the device is in the form of an ingestible capsule or other similarly sized and shaped package. Once in the stomach, it is desirable for the device to assume a substantially larger deployed state. In order to achieve the transition from a delivery state to a deployed state the device is subjected to an inflation step performed by an inflation subcomponent.

The inflation subcomponent is typically located within the volume-occupying subcomponent or integrated into the wall of the volume-occupying subcomponent. The inflation subcomponent can be self-contained, e.g., all elements necessary for inflation of the volume-occupying subcomponent are situated on or within the device at the time the patient ingests the device in the delivery state. Alternatively, in order to inflate, the inflation subcomponent can employ outside inputs such as fluids, activation agents, or externally generated signals or other forms of communication.

Preferably, the inflation subcomponent includes a mixture of solid sodium bicarbonate and solid citric acid encased within a gelatin capsule. Inflation is initiated by injecting water, preferably as an aqueous solution of citric acid, into the capsule or other structure encapsulating the gelatin capsule inflation subcomponent. An acidic aqueous solution is preferred to water or an aqueous solution at neutral or basic pH when a gelatin capsule inflation subcomponent is employed. This is because dissolution of the gelatin capsule inflation subcomponent is inhibited in acid solution, such that inflation is delayed for a suitable time period. The inflation time can also be slowed by increasing the wall thickness of the gelatin capsule; however, in order to minimize the total volume of the device, it is more desirable to employ a gelatin capsule with a thinner wall and to employ an acidic solution to delay inflation time.

The relative amounts of sodium bicarbonate and citric acid are selected so as to consume all sodium bicarbonate while minimizing the amount of solid residue after reaction. Excess sodium bicarbonate remaining in the inflated device is undesirable in that, after deflation is initiated and the wall of the device is breached, the unreacted sodium bicarbonate can result in undesirable re-inflation upon contact with acidic stomach contents. Accordingly, it is preferred to have citric acid present in a small excess. For example, the solid sodium bicarbonate and solid citric acid can be present in the capsule in a stoichiometric amount, with the injected aqueous solution of citric acid providing the excess. Alternatively, excess citric acid can be present in dry form in the capsule. It is desirable to have only a minimal excess of citric acid, so as to minimize residue remaining after reaction and to minimize the size of the inflation subcomponent. Preferably, a slight excess of citric acid is employed; however, in certain embodiments a larger excess of citric acid can be employed.

The inflation subcomponent is preferably configured to inflate while in the stomach (preferably, from about 2 minutes to about 30 minutes after injection of the device with an activating agent such as citric acid). The time to inflation is selected so as to the capsule sufficient time to pass through the esophagus, but not to enter the pylorus or small intestine before inflation occurs.

Instead of sodium bicarbonate and citric acid, other gas-generating chemical reactions can alternatively be employed, e.g., combining wax, $O_2$, and heat to form $CO_2$ and $H_2O$; combining $NaHCO_3$ and acetic acid to form $CO_2$ and $H_2O$; combining sugar and yeast to form ethanol and $CO_2$; combining $C_xH_y$, an $xO_2$, and energy to form $xCO_2$ and $yH_2O$; combining sulfur and $O_2$ to form $SO_2$; combining potassium and water to form $H_2$ and $KOH$; combining $C_6H_{12}O_6$ and yeast to form $2C_2H_5OH$ and $2CO_2$; combining cupric bicarbonate and heat to form $CuO$, water and $CO_2$; combining magnesium and $H_2SO_4$ to form $H_2$ and $MgSO_4$; combining $NaHCO_3$ and $HCl$ to form water, $CO_2$, and $NaCl$; a combustion reaction; or combining dry ice and heat to form $CO_2$.

In such embodiments it may or may not be necessary to compartmentalize or otherwise separate the components of the chemical reaction while the device is in the delivery state. For example, solid sodium bicarbonate and solid citric acid can be combined to form an inflation subcomponent mixture without the need for compartmentalization. Such a mixture is then activated upon contact with water or an aqueous solution of citric acid. When compartmentalization is employed, one skilled in the art will understand that various methods exist for temporarily separating the components, including but not limited to employing: temperature sensitive barriers, energy sensitive barriers, time sensitive barriers, light sensitive barriers, other environmentally sensitive barriers, chemically sensitive barriers, and mechanical barriers.

For example, an inflation subcomponent that includes a liquid and a solid reactant packaged into a two-part capsule can be employed. For example, the solid reactant may be in the form of a carbonate such as bicarbonate. The liquid and solid reactants are separated by a mechanical barrier present within the capsule. To initiate the chemical reaction between the liquid and the solid reactant, a force is applied to the capsule causing the capsule to break and the liquid and solid reactant to mix and react with one another. The resulting reaction produces a gas byproduct which thereby inflates the volume-occupying subcomponent with which the inflation subcomponent is associated.

It may be advantageous to delay the initiation of such reaction until the device has had sufficient time to reach the stomach. Accordingly, another embodiment of the device may contain an additional soluble barrier positioned between the solid reactant and the mechanical barrier to be broken. Such additional barrier may be, for example, a dissolvable polysaccharide or gelatin barrier that dissolves within several minutes of contact with the liquid such that inflation agents do not mix and the chemical reaction does not occur until several minutes following the breaking of the capsule.

As a further example, the volume-occupying subcomponent may be formed of a shape-memory or thermo-elastic polymer designed to assume a volume-occupying shape when in its natural, low energy state. Such a volume-occupying subcomponent may initially assume a restricted or constrained form, of a size and shape for ingestion by a patient while causing minimal discomfort, through packaging of the subcomponent into a dissolvable or biodegradable material or other container. Once the shape-memory volume-occupying subcomponent enters the stomach, the chemical or temperature environment of the stomach causes the restrictive element to break or disintegrate, by dissolution, degradation or other means, allowing the volume-occupying subcomponent to expand to its natural state. Means for restricting such shape-memory volume-occupying subcomponent include, but are not limited to, a polysaccharide capsule. Devices according to the present embodiment may, but need not necessarily employ a cover or sheath. When employed, such cover or sheath may function to create an internal cavity within the device that is isolated from the exterior environment and/or contents of the stomach. Thermo-elastic or memory shaped polymers for the above embodiments include latex, silicon, polyurethane, ethylene vinyl acetate (EVA) and ethylene vinyl alcohol (EVOH).

In certain embodiments, it may also be advantageous for the volume-occupying subcomponent to inflate gradually or in several steps over time. For example, if gas escapes the volume-occupying subcomponent prior to the desired deflation time, it would be beneficial for the device to reinflate in order to preserve it in its expanded state. To this end, in certain additional embodiments of the present invention, the volume-occupying subcomponent may contain one or more inflation subcomponents that cause the volume-occupying subcomponent to inflate gradually or in steps over time. For example, the chemical components which react with one another to inflate with the volume-occupying subcomponent may be separated in several compartments such that they will react gradually or in steps over time. For example, solid reactants and liquid may be separated by barriers designed to degrade at different times. As a further example, a first barrier may be designed to degrade several minutes following activation of the device while other barriers may be designed to degrade over the course of days, weeks or months. Such degradable barriers may be composed of any biodegradable or dissolvable material such as polyacetals or polyketals, with the degradation properties of the barrier determined by altering the composition thereof. The commencement of the barrier degradation process may be initiated by any of the trigger mechanisms described herein. Another way to achieve gradual inflation would be for one of the gas generating reactants to be produced gradually by the degradation of a precursor over time (e.g. over hours, days, weeks or months). For example, a polymer such as polylactic glycolic acid (PLGA) may be degraded over time to produce acid byproducts that react with another reactant contained in the volume-occupying subcomponent to generate gas. The commencement of the precursor degradation process may be initiated by any of the trigger mechanisms described herein.

In other embodiments, it may be desirable that once the delivered device reaches the stomach, the volume-occupying subcomponent inflates quickly to a desired size in order to reduce the danger of the volume-occupying subcomponent passing through the pyloric sphincter following delivery. To achieve such a rapid inflation, one of the inflation agents, e.g. bicarbonate, may be deployed in such a manner such as to maximize it surface area. Accordingly, upon mixing of the inflation agents, a greater amount of gas may be generated at the beginning of the reaction, resulting in a more rapid expansion of the volume-occupying subcomponent earlier following delivery. Similarly, it may be advantageous for the inflationary reactants to be engineered such that a reaction between small portions of the reactants occurs initially to help to catalyze a larger reaction between the remaining reactants. Such initial smaller reaction may also be used to cause an initial expansion of the device to dislocate or move other components within the device into a state necessary or desirable for inflation or for the device's inflated state. For example, the reactants may be constructed such that, upon initiation of the inflation step, citric acid first comes into contact with a small concentration of carbonate, triggering an initial reaction that helps to mix the remaining reactants to initiate a larger reaction. In one embodiment, the device is designed to provide for an initial smaller inflationary reaction that helps to catalyze a subsequent larger inflationary reaction and to initiate the movement of other components within the device to positions necessary or desirable for inflation or the device's inflated state. Alternatively, a reagent may be deployed so as to have an initially rapid rate of reaction and a subsequently decreasing rate. Such a variable rate of reaction and thereby inflation of the volume-occupying subcomponent may be achieved by deploying, for example, a solid reagent in the form of a compressed ball.

In another embodiment, the device may contain a wicking element in proximity to the gas generating reactants that, once in contact with a liquid reactant, serve as a medium for the liquid reactant to travel on in order to contact the solid reactant to initiate the inflation reaction. Such an embodiment would be advantageous because it would facilitate the chemical reaction by facilitating contact between reactants, and it may also enable a more complete reaction by facilitating contact between a higher proportion of the reactants than could be accomplished in the absence of the wicking element. For example, the wicking element may be composed of a hydrophilic material, such as paper, that allows a liquid reactant to travel to a solid reactant by means of capillary action. In another embodiment, the wicking element may contain or be implanted with the solid reactant on all or a part of its surface.

Deflation Subcomponents

According to the preferred embodiments, deflation of the volume-occupying subcomponent is achieved without resort to invasive procedures. Deflation subcomponents may function as a programmed time based deflation in which, after a certain period of time has lapsed since deployment or delivery of the device, the device self-deflates, without external stimulus. Alternatively, deflation may be externally triggered by a stimulus applied by the physician. Devices according to the preferred embodiments may employ a combination of the deflation subcomponents to provide greater ease of operation and greater control and safety of the device.

In a preferred embodiment the volume-occupying subcomponent may contain a biodegradable or dissolvable head that upon degradation allows fluid to escape and the volume-occupying subcomponent to deflate. The head may be constructed in such a manner that disintegration of the head materials from the volume-occupying subcomponent accelerates after a degree of degradation has occurred. For example, a first portion of the head may be designed to degrade faster than a second portion of head with the first portion stabilizing the second portion of the head such that when the first portion degrades, second portion destabilize and is released from the head, thereby accelerating the deflation process. Examples of head designs can include outer portions held together by a faster degrading centerpiece, a head with a slower degrading outer half and faster degrading inner half. An inner portion may also be partially held together by a water soluble adhesive that, upon degradation of the outer half of the head, becomes in contact with the contents of the stomach, resulting in accelerated disintegration of the inner half of the head. The deflation subcomponent may contain more than one head through which fluid is released upon deflation.

In certain preferred embodiments, the degradable head may contain materials that are degraded by enzymes that are normally present in the stomach, such as pepsin or other proteases.

Alternatively, the head may incorporate a tension element, such as a spring, a degradable link, and one or more plug elements. The degradable link serves to secure the tension element around plug element such that, upon degradation of the degradable link, tension element releases all or part of plug element from the head, thereby allowing for the escape of fluid from the volume-occupying subcomponent.

In certain alternative embodiments of the present invention, the deflation subcomponent utilizes a chemical-based technique. For example, after the device has been deployed for a specific time period within the patient, the patient will ingest a substance designed to target and degrade the material from which the volume-occupying subcomponent is formed or a sealing element incorporated within the volume-occupying subcomponent. The degrading substance may be ingested by the patient in the form of a pill, capsule, or liquid. Preferably, the degrading substance is operable to cause deflation within a predictable, short period of time (e.g., less than 24 hours, preferably less than 12 hours, less than 6 hours, less than 3 hours, or less than 1 hour) following administration of the degrading substance. For example, the all or part of the volume-occupying subcomponent wall or head may be composed of a polymer that is degraded by one or more specific enzymes or bacteria, with the degrading substance to be administered being the applicable enzyme or bacteria.

It may be advantageous to design the device in ways that improve the rate of deflation of the volume-occupying subcomponent or cause it to deflate more completely. To this end, all or part of the volume-occupying subcomponent may incorporate an elastomeric material (silicon, for example) that forms a sheath or wall that applies a contracting force on the volume-occupying subcomponent and facilitates deflation once the volume-occupying subcomponent has been breached. The contraction force applied by sheath or wall may be applied in an asymmetric manner to the volume-occupying subcomponent. For example, as the contraction force may act primarily along a longitudinal axis such that the deflated volume-occupying subcomponent has a first dimension that is greater than a second dimension.

It may be advantageous for the volume-occupying subcomponent to contain a duct valve or other type of valve that allows fluid to exit the volume-occupying subcomponent upon initiation of the deflation step but that permits little or no fluid to enter or flow back into the subcomponent.

Delivery Subcomponents

In the delivery state, devices according to the preferred embodiments employ a configuration that facilitates swallowing of the device while producing minimal discomfort to the patient. Preferably, the volume-occupying subcomponent is in a compressed configuration and other device subcomponents are sized so that the entire device may conform to the general shape of a capsule. In the delivery state, the device may be configured in any number of shapes, including the following: round, oblong, oval, suppository-shaped, mushroom-shaped, finger-shaped, bullet-shaped, or torpedo-shaped. A bullet-shaped capsule, for example, may contain the contents of the volume-occupying subcomponent more efficiently.

In a preferred embodiment, the device is fitted into a standard sized gelatin capsule. The capsule may be formed of a material that has a know rate of degradation such that the device will not be released from the capsule or otherwise deployed prior to entry into the stomach. For example, the capsule materials may include one or more polysaccharide and/or one or more polyhydric alcohols.

Alternatively, the device, in its delivery state, may be coated in a substance that confines the device in its delivery state while also facilitating swallowing. The coating may be applied by a dipping, sputtering, vapor deposition, or spraying process which may be conducted at an ambient or positive pressure.

In certain preferred embodiments, the encapsulated or coated device is lubricated or otherwise treated so as to facilitate swallowing. For example, the encapsulated or coated device may be wetted, heated, or cooled, prior to swallowing by the patient. Alternatively, the encapsulated or coated device may be dipped in a viscous substance that will serve to lubricate the device's passage through the esophagus. Examples of possible coatings would be any substances with lubricious and/or hydrophilic properties and include glycerine, polyvinylpyrrolidone (PVP), petroleum jelly, aloe vera, silicon-based materials (e.g. Dow 360) and tetrafluoroethylene (TFE). The coating may also be applied by a sputtering, vapor deposition or spraying process.

In additional embodiments the coating or capsule is impregnated or treated with one or more local anesthetics or analgesics to ease swallowing. Such anesthetics may include anesthetics in the amino amide group, such as articaine, lidocaine and trimecaine, and anesthetics in the amino ester group, such as benzocaine, procaine and tetracaine. Such analgesics may include chloraseptic.

In certain embodiments, the capsule may be weighted at a certain end in order for it to be oriented appropriately when it is administered, as it travels down the esophagus, and/or when it is in the stomach. The weighting components may include polymer materials or inflation reactants.

It may advantageous for an administrator of the device to use a delivery tool for delivering the device to the mouth or facilitating its passage through the esophagus in the optimal orientation. A delivery tool may enable the device administrator to inject the device with one or more inflation agents as the device is being administered to the patient. In a preferred embodiment, such injection may be accomplished in the same mechanical action(s) of the administrator that are employed to release the device from the delivery tool into the mouth or esophagus. For example, the delivery tool may include a plunger, a reservoir having a liquid, and an injection needle. The administrator pushes the plunger which, either in sequence or approximately simultaneously, forces the injection needle into the device and thereby injects the liquid contained in reservoir into the device. Subsequent application of force to the plunger pushes the device out of the delivery tool and into the desired location within the patient. Furthermore, the delivery tool may also include a subcomponent that administers an anesthetic or lubricant into the patient's mouth or esophagus to ease the swallowability of the device.

Volume Occupying Subcomponent

The volume-occupying subcomponent of the present invention is generally formed of a flexible material forming a wall which defines an exterior surface and an interior cavity. Various of the above-described subcomponents may be either incorporated into the wall or interior cavity of the volume-occupying subcomponent. The volume-occupying subcomponent will vary in size and shape according to the patient's internal dimensions and the desired outcome. The volume-occupying subcomponent may be engineered to be semi-compliant, allowing the volume-occupying subcomponent to stretch or expand with increases in pressure and/or temperature.

It is advantageous for the volume-occupying subcomponent wall to be both high in strength and thin, with excellent $CO_2$ retention properties. Accordingly, the volume-occupying subcomponent wall materials may be manufactured with a biaxial orientation that imparts a high modulus value to the volume-occupying subcomponent.

In one embodiment, a device according to the preferred embodiments can employ additional films or layers comprising of a polymeric substance such as polyurethane, polyethylene terephthalate, polyethylene naphthalene, polyvinyl chloride (PVC), Nylon 6, Nylon12, or polyether block amide (PEBA). The volume-occupying subcomponent may be coated with one or more additional layers of substances that aid in achieving greater gas-barrier characteristics, such as a thermoplastic substance.

Additional gas-barrier layers can also be employed in the device which have a low permeability to carbon dioxide or other fluids or gases. The barrier layers preferably exhibit good adherence to the base material. Such barrier coating materials include biocompatible poly(hydroxyamino ethers), polyethylene naphthalate, polyvinylidene chloride (PVDC), saran, polyvinyl acetate, acrylonitrile copolymers or copolymers of terephthalic acid and isophthalic acid with ethylene glycol and at least one diol. Alternative gas-barrier materials may include polyamine-polyepoxides. These materials are commonly acquired as a solvent or aqueous based thermosetting composition and are generally spray-coated onto a preform and then heat-cured to form the finished barrier coating. Alternative gas-barrier materials which may be applied as coatings to the volume-occupying subcomponent include metals such as silver or aluminum. Other materials that may be used to improve the gas impermeability of the volume-occupying subcomponent include, but are not limited to, gold or any noble metal, and PET coated with saran.

In certain preferred embodiments, the volume-occupying subcomponent includes films that are injection, blow or rotational molded. Either immediately following such molding, or after a period of curing, the gas-barrier coating may be applied.

In another embodiment, the intragastric volume-occupying subcomponent is formed using a Mylar polyester film with a coating comprising silver, aluminum or kelvalite as a metallicized surface, to improve the gas impermeability of the volume-occupying subcomponent.

In the event that the volume-occupying subcomponent's wall is composed of multiple layers of materials, it may be desirable to use certain substances or methods to connect, attach or hold together such multiple layers. Such substances can include a solvent or an ether-based adhesive. Such multiple layers may also be heat-bonded together. Once such layers are attached together to form (for example) a sheet of material to be made into a volume-occupying subcomponent, it may also be necessary to apply additional treatment steps to such material to allow it to seal together (for example, by application of a certain degree of heat and pressure) in order to be made into a volume-occupying subcomponent. Accordingly, it may be advantageous to include as an additional layer in the volume-occupying subcomponent certain materials that seal. For example, a volume-occupying subcomponent which imparts favorable mechanical and gas impermeability characteristics to the volume-occupying subcomponent may be sealed by including a layer of sealing material in such volume-occupying subcomponent.

According to another embodiment, the functionality of the volume-occupying subcomponent and the deflation component is combined either in part or in whole. For example, the volume-occupying subcomponent may be formed of a substance that is degraded within the stomach over a desired period of time. Once the degradation process has formed a breach in the wall of the volume-occupying subcomponent, the volume-occupying subcomponent deflates, continues to degrade and passes through the remainder of the digestive tract.

Preferably, an automated process is employed that takes a fully constructed volume-occupying subcomponent, evacuates all of the air within the interior cavity and folds or compresses the volume-occupying subcomponent into the desired delivery state. For example, the evacuation of air from the volume-occupying subcomponent may be actuated by vacuum or mechanical pressure (e.g. rolling the volume-occupying subcomponent). In certain embodiments, it is desirable to minimize the number of creases produced in the volume-occupying subcomponent when in the delivery state.

In another embodiment, deflation of the volume-occupying subcomponent may be achieved through one or more injection site within the wall of the volume-occupying subcomponent may be used. For example, two self-sealing injection sites can be incorporated at opposite sides of the volume-occupying subcomponent. The volume-occupying subcomponent may be positioned within a fixture that employs two small-gauge needles to evacuate the air from the volume-occupying subcomponent.

In one embodiment, the self-sealing injection sites may further be used to insert chemical elements of the inflation subcomponent into the interior of the volume-occupying subcomponent. After injection of the chemical elements into the volume-occupying subcomponent, the same needles may be used to perform evacuation of the volume-occupying subcomponent.

It may be desirable that the volume-occupying subcomponent is packed into the delivery state under, for example, a negative vacuum pressure or under a positive external pressure.

The volume-occupying subcomponent wall materials may also be engineered to, once they are initially punctured or torn, tear relatively easily from the point of such puncture or tear. Such properties would, for example, be advantageous if deflation of the volume-occupying subcomponent were initiated by a tearing or puncturing of the volume-occupying subcomponent wall, since such initial tear or puncture may then increase in scope, hastening and/or maximizing the deflation process.

The volume-occupying subcomponent may also be coated by a lubricious substance that facilitates its passage out of the body following its deflation. Examples of possible coatings would be any substances with lubricious and/or hydrophilic properties and include glycerine, polyvinylpyrrolidone (PVP), petroleum jelly, aloe vera, silicon-based materials (e.g., Dow Corning® 360 Medical Fluid; polydimethylsiloxane) and tetrafluoroethylene (TFE). The coating may be applied by a dipping, sputtering, vapor deposition or spraying process which may be conducted at an ambient or positive pressure.

Tracking and Visualization Subcomponent

It may also be beneficial to implement tracking and visualization functionality into devices according to the preferred embodiments. Due to the non-invasive nature of the present device, physicians may desire to determine, or confirm, the location and orientation of the device prior to inflation or during the course of treatment.

In one embodiment, the volume-occupying subcomponent incorporates a barium sulfate or other radioopaque marker, e.g., a metal component such as a metal ring. The marker may be implemented so as to form an identifiable geometric pattern on the inflated volume-occupying subcomponent when imaged or otherwise viewed on x-ray or other visualization equipment. For example, the marker may form a circular stripe at the equator and/or a stripe around each pole of the volume-occupying subcomponent. When the markers form expanded circles and are positioned relatively far apart, this indicates that the volume-occupying subcomponent is in the deployed or inflated state. When the markers form condensed circles positioned relatively close together, this indicates that the volume-occupying subcomponent is in a deflated state. The distance between the markers indicates the degree to which the volume-occupying subcomponent is inflated.

Alternatively, the marker may be applied to the volume-occupying subcomponent when the volume-occupying subcomponent is in a creased or folded state such that when the volume-occupying subcomponent is in its deflated state the marker appears concentrated when viewed on visualization equipment, and when the volume-occupying subcomponent is inflated the marker appears less concentrated when viewed on visualization equipment. Alternatively, the marker may be applied or incorporated into the volume-occupying subcomponent so as to facilitate identification and location of the various subcomponents of the device, such as a valve, head, or weight. The marker may be printed or painted onto a surface of the volume-occupying subcomponent or between layers of the material forming the volume-occupying subcomponent. Alternatively, a metal coating as described below may be used as a marker to identify and/or locate the volume-occupying subcomponent. Metal coatings for visualizing the volume-occupying subcomponent may include silver, gold, tantalum or any noble metal. Alternatively, the marker may be applied to an elastomeric sleeve that covers all or part of the volume-occupying subcomponent.

In another embodiment, the volume-occupying subcomponent incorporates a subcomponent that changes mechanically upon inflation of the volume-occupying subcomponent, which mechanical change can be visualized using x-ray or other visualization equipment. For example, a mechanical portion of the volume-occupying subcomponent containing a visualization marker may elongate upon an increase in pressure in the volume-occupying subcomponent.

Alternatively, a marker may be formed using a metalized mesh located between layers of the material from which the volume-occupying subcomponent is constructed. The pattern or patterns formed by the imbedded marker will appear when the volume-occupying subcomponent is in an inflated, deployed state.

It is envisioned that marker materials may be incorporated into the volume-occupying subcomponent to facilitate various visualization techniques such as, for example, MRI, CT and ultrasound.

The volume-occupying subcomponent may also contain a dye or marker that is released upon deflation to indicate that the volume-occupying subcomponent cavity has been breached. Such dye or marker may, for example, be apparent in the patient's urine as an indication that the volume-occupying subcomponent has begun to deflate.

In yet further embodiments, mechanical, chemical, visual and other sensors may be included as part of the device to measure, record and/or transmit information relating to the device and/or the patient's internal environment. For example, the device may contain a camera or any of the other imaging and transmission components of a Pillcam device. As an additional example, the device may contain sensors that measure, record and/or transmit information relating to stomach pH, stomach pressure, hormone levels, organ health, and organ safety.

Drug Delivery Component

It is also envisioned that the device of the present invention may further achieve the objective of delivering and administering various pharmaceutical therapies and treatments. Pharmaceutical substances may be incorporated into the material forming the volume-occupying subcomponent, into degradable pockets formed on the interior or exterior surfaces of the volume-occupying subcomponent, and/or coated on the outside of the volume-occupying subcomponent. Alternatively or additionally, pharmaceutical substances may be incorporated into or on one or more of the various other subcomponents of the device.

Different drugs may be applied in different regions on the surface of the volume-occupying subcomponent. Alternatively, the outside of the volume-occupying subcomponent may be comprised of a microporous or meshed exterior designed to facilitate deposition and release of drug materials. A volume-occupying subcomponent containing a mesh or microsphere like surface where drugs may be deposited or embedded can be employed.

In certain embodiments, the volume-occupying subcomponent may contain pharmaceutical substances in an interior cavity which can be subsequently released. The volume-occupying subcomponent can contain a drug in a subcompartment of the volume-occupying subcomponent that is adjacent to the head. Release of the drug from subcompartment may be achieved by any number of means such as by a pump, valve or head breakage.

Alternatively, inflation subcomponent may be configured to gradually release pharmaceutical substances as the head component(s) disintegrate or in bulk when the head component separates from the volume-occupying subcomponent. For example, a pharmaceutical may be fixed in biodegradable plug materials and released as such materials degrade in the stomach. Such substances may be incorporated or implanted into a polymer (e.g. by means of diffusion or hydrolysis) which can be sprayed, sputter coated, vapor deposited or applied in liquid form onto the outside of the volume-occupying subcomponent.

Furthermore, pharmaceutical substances may also be incorporated into one or more of the barrier coatings of the volume-occupying subcomponent or a lubricious coating applied to the volume-occupying subcomponent. Release of the drug may, for example, be modulated by diffusion of the drug from the coating or by degradation of the coating itself, resulting in the release of the drug. The release or diffusion properties of the drug may be influenced by modifying the characteristics of the polymer, such as by changing the ratio of hydrophobic to hydrophilic molecules in the composition of the polymer. Release of drug may also be modulated by electrophoresis actuated by remotely by an external source.

It may be advantageous to treat the volume-occupying subcomponent such that its outer layer has antimicrobial properties so that it may treat or prevent stomach infections. For example, certain portions of the outer layer of the volume-occupying subcomponent may contain silver. As a further example, the outer layer of the volume-occupying subcomponent may be made of a material (such as polyurethane) that allows for ion transfer across of it, with silver materials behind such layer such that the silver ions are able to diffuse out of the volume-occupying subcomponent or onto its exterior surface.

For example, the volume-occupying subcomponent may be coated with a drug, or combination of drugs, to control stomach acid and other gastrointestinal conditions such as ulcers and gastroesophageal reflux disease (GERD). The drugs may, but need not be selected from the group of drugs including proton pump inhibitors such as Prilosec (omeprazole), Nexium (esomeprazole), Prevacid (lansoprazole), Protonix (pantoprazole) and Aciphex (rabeprazole) or $H_2$ receptor antagonists such as Tagamet (cimetidine), Pepcid (famotidine), Axid (nizatidine), Zantac (ranitidine) and Rotane (roxatadine).

The volume-occupying subcomponent may be treated with anti-emetics drug or combinations of anti-emetics to control nausea and vomiting including, but not limited to, 5HT3 antagonists such as compazine, dolasetron, granisetron, ondansetron, tropisetron, palonosetron or dopamine antagonists such as domperidone, droperidol, haloperidol, chlorpromazine, promethazine, prochlorperazine, metoclopramide, alizapride or antihistamines (H1 receptor antagonists) such as cyclizine, diphenhydramine, dimenhydrinate, meclizine, promethazine, hydroxyzine or cannabinoids.

The volume-occupying subcomponent may be coated with drugs or combinations of drugs to control body weight including serotonin re-uptake inhibitors (e.g., fluoxetine), noradrenergic re-uptake inhibitors (e.g., phentermine), a serotonin and noradrenergic re-uptake inhibitor (sibutramine) and an intestinal lipase inhibitor (orlistat), Leptin, amylin, melanocortin-4 receptor agonists, neuropeptide Y antagonists, beta(3) adrenergic agonists and glucagon-like peptide-1 agonists and CB1 endocannabinoid receptor antagonists and CNS modulators that mediate appetite and energy expenditure.

The volume-occupying subcomponent may also be coated with drugs or combinations of drugs to control blood glucose levels including but not limited to sulfonylureas, meglitinides, nateglinides, biguanides, thiazolidinediones, and alpha-glucose inhibitors.

Example drugs may also include satiety signaling substances or substances that modulate hormone levels.

Example drugs may also include laxative agents. Such laxative agents may be useful in facilitating the passage of the volume-occupying subcomponent from the body when it is in its deflated state.

Example drugs may also include substances that modulate gastric emptying such as cholestyramine, or that modulate gastric absorption.

Example drugs may also include analgesics such as acetaminophen, the non-steroidal anti-inflammatory drugs (NSAIDs) such as the salicylates and narcotic drugs such as morphine.

Example drugs may also include substances that reduce nicotine and/or tobacco craving such as varenicline, bupropion and nortriptyline.

Example drugs may also include birth control substances such as combinations of estrogen and progestin, and selective estrogen receptor modulators.

Example drugs may also include antibiotics or other antibacterial substances.

Example drugs may also include antacids.

An alternative to a coated volume-occupying subcomponent is a volume-occupying subcomponent containing reservoirs that contain the pharmaceutical of interest. For example, the present invention provides a volume-occupying device that could be used as a subcomponent for delivering drugs to the stomach, possibly including a framework with a plurality of reservoirs and a drug polymer or combination of drug polymers positioned in the reservoirs. In one embodiment, a plurality of microcapsules on the exterior of said volume-occupying subcomponent, each of said microcapsules carrying a drug or combination of drugs for treatment with the stomach when said volume-occupying subcomponent, is positioned and inflated such that the drug or drugs may be released from said microcapsules.

A possible alternative to a coated volume-occupying subcomponent is a volume-occupying subcomponent containing the pharmaceutical of interest in its plug materials. Any of the means to initiate deflation described above may be used to modulate erosion or breakage of the plug materials to initiate release of drug substance.

A possible alternative to a coated volume-occupying subcomponent is a volume-occupying subcomponent containing the pharmaceutical of interest in its creases when it is in is delivery form, with release of the drug initiated by expansion of the volume-occupying subcomponent.

A possible alternative to a coated volume-occupying subcomponent is a volume-occupying subcomponent containing the pharmaceutical of interest in its cavity. Release of the drug may be modulated by a pump that may be actuated as described above.

The drug delivery components of the volume-occupying subcomponent may be designed in such way as to incorporate multiple drugs and to release select drugs upon command. For example, drugs may be layered on top of one another or adjacent to each other on certain portions of the volume-occupying subcomponent.

The contents of the following publications, which recite methods of controlled drug delivery are hereby incorporated into this application by reference: Langer, R. (1998) "Drug Delivery and Targeting," Nature vol. 392/Supp, pp. 5-10; Controlled Drug Delivery Systems, Xue Shen Wu, PhD., Technomic Publishing Co, 1996.

Alternatively, the volume-occupying subcomponent may contain a subcomponent that may electro-modulate certain nerves in the stomach (such as the vagus nerve) to induce satiety. Such subcomponent may be recharged inductively by an exterior power source.

Composite Wall for Balloon

A self-inflatable gastric balloon inflated by $CO_2$ gas employs a composite wall that provides barrier properties ($CO_2$ retention), properties imparting resistance to pH and moisture conditions in the gastric environment or the environment within the central lumen of the balloon, and structural properties to resist gastric motility forces, abrasion of the balloon wall in vivo, and damage during manufacturing and folding of the balloon. Certain materials employed in the balloon materials are able to withstand a hostile gastric environment designed to break down foreign objects (e.g., food particles). Some of the variables that the gastric environment encompasses are as follows: gastric liquid pH of from 1.5-5; temperature of approx. 37° C.; a relative humidity of 100%; and constant gastric motility external pressures of from 0-4 psi at variable frequencies and cycle times based on the fed state of the stomach. The external pressure imparted by gastric motility can also cause abrasions on the surface of the balloon. The inside of the balloon lumen is slightly acidic and contains moisture from the aqueous solution injected to activate the $CO_2$ generation reaction ("activation agent") and therefore the innermost layers of the balloon wall must be able to withstand moisture and acidity as well as retain the $CO_2$ gas. In addition to these environmental stresses the wall materials meet biocompatibility requirements and are constructed such that the total thickness of the wall (barrier material) is thin enough to be folded and placed inside of a container ("outer container") without significant damage. The outer container also holds the capsule that contains the $CO_2$ generator ("inner container"). The outer container is small enough to transcend the esophagus (having a diameter of approximately 2.5 cm). The wall or barrier material is also heat sealable for balloon manufacture/formation and maintains a bond strength that can contain internal pressures of up to 4 psi generated by the $CO_2$ reaction during self-inflation. The film properties that are evaluated to determine suitability for use in the composite wall of the balloon include pH resistance, water vapor transmission rate, $CO_2$ barrier properties, mechanical strength/abrasion properties, temperature Resistance, flex-crack (Gelbo) resistance, surface energy (wettability) compliance, and heat bond potential.

The various layers in the composite wall can impart one or more desirable properties to the balloon (e.g., $CO_2$ retention, resistance to moisture, resistance to acidic environment, wettability for processing, and structural strength). A list of polymer resins and coatings that can be combined into a multi-layer preformed system ("composite wall") is provided in Table 1. These films can be adhesively bonded together, co-extruded, or adhered via tie layers or a combination thereof to obtain the desired combination of properties for the composite wall, as discussed below. The materials identified as film coatings in Table 1 are provided as coatings applied to a base polymer film, e.g., PET, or other structural layer.

TABLE 1

Polymer Film and Coating Materials

| | Characteristics | | |
|---|---|---|---|
| | Good Structural/Behavior/Mechanical Strength/Compliance | Good $CO_2$ Barrier Properties | Good Manufacturability/Surface Energy Properties |
| FILM RESINS | | | |
| Polyethylene Terephthalate (PET) | X | X | |
| Polytrimethylene Terephthalate (PTT) | | | |
| Liquid Crystal Polymer (LCP) | X | X | |
| Polytrimethylene naphthalate (PTN) | X | X | |
| Polyethylene naphthalate (PEN) | X | X | |
| Polyimide (PI) | X | X | |
| Linear Low Density Polyethylene (LLDPE) | | | X |
| Ethylene Vinyl Alcohol (EVOH) | | X | |
| Polyamide: Nylon (PA) and Nylon-6 (PAG)/Nylon 12 | | X | X |
| High Density Polyethylene (HDPE) | | | X |
| Polypropylene (PP) | | | X |
| Polyurethane | | | X |
| PVDC (Saran) | | X | X |
| Polyether Block Amide (Pebax) | | | X |
| Polyvinyl Alcohol (PVOH) | | X | |
| Silicone | X | | X |
| FILM COATINGS | | | |
| Silicone Dioxide (SiO2) | | X | |
| Aluminum Oxide ($Al_2O_3$) | | X | |
| Nanopolymers (Nano/Clay) | | X | |
| External Organic Coatings (e.g., epoxy amine) | | X | |
| Inorganic Coatings (e.g., Amorphous Carbon) | | X | |
| Oxygen Scavengers | | X | |
| Parylene C | | X | |

$CO_2$ Retention Layers

In preferred embodiments, a blended polymer resin using multiple layers is employed to maintain the inflated balloon's shape and volume by retaining $CO_2$ gas for the duration of the intended use. Certain barrier films, widely used in the food packaging and plastic bottling industries, can advantageously be employed for this purpose in the composite wall of the balloon. Preferably, the $CO_2$-barrier materials have a low permeability to carbon dioxide (or other gases, liquids, or fluids that are alternatively or additionally used to inflate the volume-occupying subcomponent). These barrier layers preferably have good adherence to the base material. Preferred barrier coating materials and films include polyethylene terephthalate (PET), linear low density polyethylene (LLDPE), ethylene vinyl alcohol (EVOH), polyamides such as Nylon (PA) and Nylon-6 (PA-6), polyimide (PI), liquid crystal polymer (LCP), high density polyethylene (HDPE), polypropylene (PP), biocompatible poly(hydroxyamino ethers), polyethylene naphthalate, polyvinylidene chloride (PVDC), saran, ethylene vinyl alcohol copolymers, polyvinyl acetate, silicon oxide (SiOx), silicon dioxide ($SiO_2$), aluminum oxide ($Al_2O_3$), polyvinyl alcohol (PVOH), nanopolymers (e.g., nanoclay), polyimide thermoset film, EVALCA EVAL EF-XL, Hostaphan GN, Hostaphan RHBY, RHB MI, Techbarrier HX (SiOx-coated PET), Triad Silver (silver metallized PET), Oxyshield 2454, Bicor 84 AOH, acrylonitrile copolymers, and copolymers of terephthalic acid and isophthalic acid with ethylene glycol and at least one diol. Alternative gas-barrier materials include polyamine-polyepoxides. These materials are typically provided as a solvent-based or aqueous-based thermosetting composition and are typically spray-coated onto a preform and then heat-cured to form the finished barrier coating. Alternative gas barrier materials that can be applied as coatings to the volume-occupying subcomponent include metals such as silver or aluminum. Other materials that may be used to improve the gas impermeability of the volume occupying subcomponent include, but are not limited to, gold or any noble metal, PET coated with saran, and conformal coatings.

One method that is used in the packaging industry to delay diffusion of $CO_2$ is to thicken the material so as to increase the time between the sorption and desorption phases of $CO_2$ (see FIG. 1). Increasing the internal pressure of the balloon also delays the mass transfer process. Thickening the material is generally not preferred, as the total composite wall thickness preferably does not exceed 0.0025 inches (0.00635 cm) in order for the balloon to be foldable into the desired delivery container size for swallowing by a patient.

A multilayer polymer film that is able to withstand the gastric environment over the course of the usable life of the balloon includes linear low density polyethylene (LLDPE) adhesively bonded to a polyethylene terephthalate (PET) coated silicon oxide (SiOx) film. However, the flex-crack resistance of the SiOx-coated film is poor due to the crystalline structure of SiOx, and therefore the film's susceptibility to damage during the manufacturing and compacting process is high. Controlling the thickness of the SiOx applied is a mechanism to enhance CO2 diffusion resistance; however, the thickness of SiOx applied preferably does not exceed 800 angstroms. Alternatively, an additional film layer with $CO_2$ barrier properties, such as ethylene vinylalcohol—polyethylene (EVOH-PE) or PET coated with a $CO_2$ barrier layer (e.g., a metal, nanoclay particles, or aluminum oxide) can be added to the composite wall.

The layers providing gas ($CO_2$) barrier properties are preferably situated as inner layers in the composite wall.

Structural Layers

Layers such as polyurethane or polyethylene terephthalate (PET) can be added to the composite wall for structural purposes, and are preferably placed as outermost (proximal to the gastric environment or proximal to the central lumen of the balloon) layers, provided that the pH resistance of such layers can withstand the acidic environment of the stomach or the central lumen of the balloon.

Polyethylene Terephthalate (PET)

Polyethylene terephthalate is a thermoplastic polymer resin of the polyester family. Polyethylene terephthalate may exist as an amorphous (transparent) or as a semi-crystalline material. The semi-crystalline material can appear transparent (spherulites<500 nm) or opaque and white (spherulites up to a size of some μm) depending on its crystal structure and spherulite size. Its monomer (bis-ß-hydroxyterephthalate) can be synthesized by the esterification reaction between terephthalic acid and ethylene glycol with water as a byproduct, or by transesterification reaction between ethylene glycol and dimethyl terephthalate with methanol as a byproduct. Polymerization is through a polycondensation reaction of the monomers (done immediately after esterification/transesterification) with ethylene glycol as the byproduct (the ethylene glycol is directly recycled in production). Some of the trade names of PET products are Dacron, Diolen, Tergal, Terylene, and Trevira fibers, Cleartuf, Eastman PET and Polyclear bottle resins, Hostaphan, Melinex, and Mylar films, and Arnite, Ertalyte, Impet, Rynite and Valox injection molding resins.

PET consists of polymerized units of the monomer ethylene terephthalate, with repeating $C_{10}H_8O_4$ units. PET can be semi-rigid to rigid, depending on its thickness, and is very lightweight. It makes a good gas and fair moisture barrier, as well as a good barrier to alcohol and solvents. It is strong and impact-resistant. It is naturally colorless with high transparency.

When produced as a thin film (biaxially oriented PET film, often known by one of its tradenames, "Mylar"), PET can be aluminized by evaporating a thin film of metal onto it to reduce its permeability, and to make it reflective and opaque (MPET). These properties are useful in many applications, including flexible food packaging. When filled with glass particles or fibers, it becomes significantly stiffer and more durable. This glass-filled plastic, in a semi-crystalline formulation, is sold under the tradename Rynite, Arnite, Hostadur, and Crastin.

One of the most important characteristics of PET is intrinsic viscosity. The intrinsic viscosity of the material, measured in deciliters per gram (dl/g) is dependent upon the length of its polymer chains. The longer the chains, the stiffer the material, and therefore the higher the intrinsic viscosity. The average chain length of a particular batch of resin can be controlled during polymerization. An intrinsic viscosity of about: 0.65 dl/g-0.84 dl/g is preferred for use in a composite wall.

In addition to pure (homopolymer) PET, PET modified by copolymerization is also available. In some cases, the modified properties of copolymer are more desirable for a particular application. For example, cyclohexane dimethanol (CHDM) can be added to the polymer backbone in place of ethylene glycol. Since this building block is much larger (6 additional carbon atoms) than the ethylene glycol unit it replaces, it does not fit in with the neighboring chains the way an ethylene glycol unit would. This interferes with crystallization and lowers the polymer's melting temperature. Such PET is generally known as PETG (Eastman Chemical and SK Chemicals are the only two manufacturers). PETG is a clear amorphous thermoplastic that can be injection molded or sheet extruded. It can be colored during processing. Another common modifier is isophthalic acid, replacing some of the 1,4-(para-) linked terephthalate units. The 1,2-(ortho-) or 1,3-(meta-) linkage produces an angle in the chain, which also disturbs crystallinity. Such copolymers are advantageous for certain molding applications, such as thermoforming. On the other hand, crystallization is important in other applications where mechanical and dimensional stability are important. For PET bottles, the use of small amounts of CHDM or other comonomers can be useful: if only small amounts of comonomers are used, crystallization is slowed but not prevented entirely. As a result, bottles are obtainable via stretch blow molding ("SBM"), which are both clear and crystalline enough to be an adequate barrier to aromas and gases such as carbon dioxide in carbonated beverages.

Crystallization occurs when polymer chains fold up on themselves in a repeating, symmetrical pattern. Long polymer chains tend to become entangled on themselves, which prevents full crystallization in all but the most carefully controlled circumstances. 60% crystallization is the upper limit for commercial products, with the exception of polyester fibers.

PET in its natural state is a crystalline resin. Clear products can be produced by rapidly cooling molten polymer to form an amorphous solid. Like glass, amorphous PET forms when its molecules are not given enough time to arrange themselves in an orderly fashion as the melt is cooled. At room temperature the molecules are frozen in place, but if enough heat energy is put back into them, they begin to move again, allowing crystals to nucleate and grow. This procedure is known as solid-state crystallization.

Like most materials, PET tends to produce many small crystallites when crystallized from an amorphous solid, rather than forming one large single crystal. Light tends to scatter as it crosses the boundaries between crystallites and the amorphous regions between them. This scattering means that crystalline PET is opaque and white in most cases. Fiber drawing is among the few industrial processes that produces a nearly single-crystal product.

Comonomers such as CHDM or isophthalic acid lower the melting temperature and reduces the degree of crystallinity of PET (especially important when the material is used for bottle manufacturing). Thus the resin can be plastically formed at lower temperatures and/or with lower force. This helps to prevent degradation, reducing the acetaldehyde content of the finished product to an acceptable (that is, unnoticeable) level. Other ways to improve the stability of the polymer is by using stabilizers, mainly antioxidants such as phosphites. Recently, molecular level stabilization of the material using nanostructured chemicals has also been considered.

Unreinforced PET has the following properties: Bulk Density 0.800-0.931 g/cc; Density 1.10-1.20 g/cc @Temperature 285-285° C.; 1.25-1.91 g/cc; Apparent Bulk Density 0.000850 g/cc; Water Absorption 0.0500-0.800%; Moisture Absorption at Equilibrium 0.200-0.300%; Water Absorption at Saturation 0.400-0.500%; Particle Size 2500 μm; Water Vapor Transmission 0.490-6.00 g/m$^2$/day; Oxygen Transmission 5.10-23.0 cc-mm/mg-24 hr-atm; Viscosity Measurement 0.550-0.980; Viscosity Test 74.0-86.0 cm$^3$/g; Thickness 250-254 microns; Linear Mold Shrinkage 0.00100-0.0200 cm/cm; Linear Mold Shrinkage, Transverse 0.00200-0.0110 cm/cm; Hardness, Rockwell M 80.0-95.0; Hardness, Rockwell R 105-120 105-120; Ball Indentation Hardness 160-170 MPa; Tensile Strength, Ultimate 22.0-207 MPa; Film Tensile Strength at Yield, MD 55.0-59.0 MPa; Film Tensile Strength at Yield, TD 53.0-57.0 MPa; Film Elongation at Break, MD 40.0-600%; Film Elongation at Break, TD 200-600%; Film Elongation at Yield, MD 4.00-6.00%; Film Elongation at Yield, TD 4.00-6.00%; Tensile Strength, Yield 47.0-90.0 MPa; Elongation at Break 1.50-600%; Elongation at Yield 3.50-30.0%; Modulus of Elasticity 1.83-14.0 GPa; Flexural Modulus 1.90-15.2 GPa; Flexural Yield Strength 55.0-240 MPa; Compressive Yield Strength 20.0-123 MPa; Izod Impact, Unnotched 2.67 J/cm—NB; Izod Impact, Unnotched Low Temp (ISO) 160-181 kJ/m$^2$; Izod Impact, Notched, Low Temp (ISO) 3.10-4.20 kJ/m$^2$; Charpy Impact Unnotched 3.00 J/cm$^2$—NB; Charpy Impact, Notched, Low Temp 0.270-0.500 J/cm$^2$; Charpy Impact, Notched 0.200-1.40 J/cm$^2$; Impact Test 0.800-8.20 J @Temperature −40.0° C.; Coefficient of Friction 0.190-0.250; Tear Strength, Total 15.0-120 N; Elmendorf Tear Strength, MD 3.14-4.00 g/micron; Elmendorf Tear Strength, TD 3.24-5.20 g/micron; Dart Drop 1.08-2.00 g/micron; Taber Abrasion, mg/1000 Cycles; Film Tensile Strength at Break, MD 13.8-60.0 MPa; Film Tensile Strength at Break, TD 39.0-48.0 MPa; Izod Impact, Notched @−40° C. 0.270-0.630 J/cm; Izod Impact, Notched 0.139-100 J/cm; Izod Impact, Notched (ISO) 2.00-10.0 kJ/m$^2$; Electrical Resistivity 5.00e+6-1.00e+16 ohm-cm; Surface Resistance 1.00e+14-1.00e+16 ohm; Dielectric Constant 2.40-3.90; Dielectric Strength 15.7-60.0 kV/mm; Dissipation Factor 0.00100-0.0250; Arc Resistance 80.0-181 sec; Comparative Tracking Index 175-600 V; Heat of Fusion 56.0-65.0 J/g; CTE, linear 25.0-92.0 μm/m-° C.; CTE, linear, Transverse to Flow 48.0-80.0 μm/m-° C.; Specific Heat Capacity 1.10-1.20 J/g-° C.; 1.30-2.30 J/g-° C. @Temperature 60.0-280° C.; Thermal Conductivity 0.190-0.290 W/m-K; Melting Point 200-255° C.; Maximum Service Temperature, Air 100-225° C.; Deflection Temperature at 0.46 MPa (66 psi) 66.0-245° C.; Deflection Temperature at 1.8 MPa (264 psi) 60.0-240° C.; Vicat Softening Point 74.0-85.0° C.; Minimum Service Temperature, Air −20.0° C.; Glass Temperature 70.0-78.0° C.; UL RTI, Electrical 75.0-175° C.; Haze 0.300-10.0%; Gloss 108-166%; Transmission, Visible 67.0-99.0%; Gardner Color Number −3.00-85.0; Processing Temperature 120-295° C.; Mold Temperature 10.0-163° C.; Drying Temperature 70.0-160° C.; Dry Time 3.00-8.00 hour; Moisture Content 0.0100-0.400%; Injection Pressure 68.9-120 MPa; Back Pressure 8.00-18.0 MPa.

Polyethylene terephthalate films are available from Mitsubishi Polyester Film of Wiesbaden, Germany under the tradename Hostaphan(r). Hostaphan(r) GN is a glass clear biaxially oriented film, made of polyethylene terephthalate (PET) and is characterized by its high transparency and surface gloss and its low haze accompanied by its excellent mechanical strength and dimensional stability. Hostaphan(r) GN is one or two side chemically treated for improved slip and processability as well as for improvement of the adhesion of coatings, printing inks or metallic layers. Hostaphan (r) RHBY is a biaxially oriented film made of polyethylene terephthalate (PET) with a structure optimized to offer previously unattainable barrier properties against oxygen, water vapor and other gases as well as aroma substances after vacuum coating with aluminum, $Al_2O_3$ or SiOx.

Linear Low-Density Polyethylene (LLDPE)

Linear low-density polyethylene (LLDPE) is a substantially linear polymer (polyethylene), with significant numbers of short branches, commonly made by copolymerization of ethylene with longer-chain olefins. Linear low-density polyethylene differs structurally from conventional low-density polyethylene because of the absence of long chain branching. The linearity of LLDPE results from the different manufacturing processes of LLDPE and LDPE. In general, LLDPE is produced at lower temperatures and pressures by copolymerization of ethylene and such higher alpha olefins as butene, hexene, or octene. The copolymerization process produces an LLDPE polymer that has a narrower molecular weight distribution than conventional LDPE and in combination with the linear structure, significantly different rheological properties.

The production of LLDPE is initiated by transition metal catalysts, particularly Ziegler or Philips type of catalyst. The actual polymerization process can be done in either solution phase or gas phase reactors. Usually, octene is the copolymer in solution phase while butene and hexene are copolymerized with ethylene in a gas phase reactor. The LLDPE resin produced in a gas phase reactor is in granular form and may be sold as granules or processed into pellets. LLDPE has higher tensile strength and higher impact and puncture resistance than LDPE. It is very flexible and elongates under stress. It can be used to make thinner films, with better environmental stress cracking resistance. It has good resistance to chemicals and to ultraviolet radiation. It has good electrical properties. However it is not as easy to process as LDPE, has lower gloss, and narrower range for heat sealing.

LDPE and LLDPE have unique theoretical or melt flow properties. LLDPE is less shear sensitive because of its narrower molecular weight distribution and shorter chain branching. During a shearing process, such as extrusion, LLDPE remains more viscous, therefore harder to process than an LDPE of equivalent melt index. The lower shear sensitivity of LLDPE allows for a faster stress relaxation of the polymer chains during extrusion and therefore the physical properties are susceptible to changes in blow-up ratios. In melt extension, LLDPE has lower viscosity at all strain rates. This means it will not strain harden the way LDPE does when elongated. As the deformation rate of the polyethylene increases, LDPE demonstrates a dramatic rise in viscosity because of chain entanglement. This phenomena is not observed with LLDPE because of the lack of long-chain branching in LLDPE allows the chains to "slide by" one another upon elongation without becoming entangled. This characteristic is important for film applications because LLDPE films can be downgauged easily while maintaining high strength and toughness.

Properties of film grade LLDPE include: Density 0.902-0.960 g/cc; Moisture Vapor Transmission 0.240-0.470 cc-mm/mg-24 hr-atm; Water Vapor Transmission 6.00-8.00 g/m$^2$/day; Oxygen Transmission 0.720-236 cc-mm/mg-24 hr-atm; Oxygen Transmission Rate 3500-5000 cc/m$^2$/day; Viscosity 37000-79000 cP @Temperature 190-190° C.; 37000-79000 cP @Shear Rate 300-5000 l/s; 37000-79000 cP @Shear Rate 300-5000 l/s; Thickness 12.7-76.2 microns; Melt Flow 0.200-40.0 g/10 min; Base Resin Melt Index 0.700-3.50 g/10 min; Antiblock Level 3500-9000 ppm; Slip Level 0.000-1700 ppm; Tensile Strength, Ultimate 9.80-26.2 MPa; Film Tensile Strength at Yield, MD 7.38-74.0 MPa; Film Tensile Strength at Yield, TD 6.90-77.0 MPa; Film Elongation at Break, MD 80.0-1460%; Film Elongation at Break, TD 460-1710%; Film Elongation at Yield, MD 435-640%; Film Elongation at Yield, TD 670-890%; Tensile Strength, Yield 9.70-22.1 MPa; Elongation at Break 8.00-1000%; Modulus of Elasticity 0.0110-0.413 GPa; Secant Modulus, MD 0.0103-0.717 GPa; Secant Modulus, TD 0.0106-0.869 GPa; Impact 48.0-65.0; Impact Test 0.452-5.00 J; Coefficient of Friction 0.100-2.00; Coefficient of Friction, Static 0.170-1.00; Elmendorf Tear Strength MD 25.0-1080 g 2; Elmendorf Tear Strength TD 180-1470 g; Elmendorf Tear Strength, MD 0.0750-20.9 g/micron; Elmendorf Tear Strength, TD 0.275-37.8 g/micron; Dart Drop 1.57-42.5 g/micron; Dart Drop Test 30.0-1350 g; Seal Strength 1800-2400 g/25 mm; Film Tensile Strength at Break, MD 9.65-82.7 MPa; Film Tensile Strength at Break, TD 7.24-55.1 MPa; Heat Seal Strength Initiation Temperature 72.0-100° C.; Melting Point 120-128° C.; Crystallization Temperature 104-115° C.; Vicat Softening Point 93.0-123° C.; Haze 0.700-80.0%; Gloss 3.00-140%; Processing Temperature 90.0-310° C.; Die Opening 0.0810-0.254 cm; Blow-up Ratio (BUR) 1.50-4.00.

Ethylene Vinyl Alcohol (EVOH)

Ethylene Vinyl Alcohol is a formal copolymer of ethylene and vinyl alcohol. Because the latter monomer mainly exists as its tautomer acetaldehyde, the copolymer is prepared by polymerization of ethylene and vinyl acetate followed by hydrolysis. The plastic resin is commonly used in food applications, and in plastic gasoline tanks for automobiles. Its primary purpose is to provide barrier properties, primarily as an oxygen barrier for improved food packaging shelf life and as a hydrocarbon barrier for fuel tanks. EVOH is typically coextruded or laminated as a thin layer between cardboard, foil, or other plastics. EVOH copolymer is defined by the mole % ethylene content: lower ethylene content grades have higher barrier properties; higher ethylene content grades have lower temperatures for extrusion.

Ethylene Vinyl Alcohol (EVOH) is one of the most common clear high barrier films used today. It is applied as a discrete layer in a coextrusion. EVOH provides excellent oxygen barrier properties (0.006-0.12 cc-mil/100 in$^2$-day). The barrier that a particular EVOH film provides is dependent upon a number of factors: mole percent—as the ethylene mole percent increases, the barrier decreases; degree of crystallinity—as the degree of crystallinity increases, the barrier properties improve; thickness—as with all films, as the thickness increases, the barrier increases; temperature—as the temperature increases, the barrier decreases; humidity—at high humidity levels, the barrier provided by EVOH drops rapidly (it is the humidity level at the EVOH interface rather than ambient humidity that is critical). In addition to providing an excellent oxygen barrier, EVOH is also an excellent odor and aroma barrier. It has the added advantage of being thermoformable making it popular for 3D applications.

EVALCA EVAL® EF-XL Ethylene Vinyl Alcohol Copolymer Film has the following properties: Moisture Vapor Transmission 0.600 cc-mm/mg-24 hr-atm 40° C., 90% RH; Oxygen Transmission 0.00400 cc-mm/mg-24 hr-atm 20° C.; 65% RH (permeability increases significantly at higher moisture content); thickness 15.2 microns; Film Elongation at Break, MD 100% 10%/min.; ASTM D638 Film Elongation at Break, TD 100% 10%/min.; ASTM D638 Secant Modulus, MD 3.50 GPa; Youngs Modulus, ASTM D638, 10%/min.; Secant Modulus, TD 3.50 GPa; Youngs Modulus, ASTM D638, 10%/min.; Elmendorf Tear Strength MD 260 g; ASTM D638 Elmendorf Tear Strength TD 330 g; ASTM D638 Elmendorf Tear Strength, MD 17.0 g/micron; ASTM D638 Elmendorf Tear Strength, TD 21.7 g/micron; ASTM D638 Film Tensile Strength at Break, MD 205 MPa 10%/min.; ASTM D638 Film Tensile Strength at Break, TD 195 MPa 10%/min.; Surface Resistance 2.70e+15 ohm; Dielectric Constant 5.00; Dissipation Factor 0.220; Specific Heat Capacity 2.40 J/g-° C.; Thermal Conductivity 0.340 W/m-K; Melting Point 181° C. DSC; Haze 0.500% 65% RH; Gloss 95.0% 65% RH. EVAL® ethylene vinyl alcohol films are available from Kuraray America, Inc. of Houston, Tex.

Nylon

Nylon is a generic designation for a family of synthetic polymers known generically as polyamides. Nylon is a thermoplastic silky material. There are two common methods of making nylon for fiber applications. In one approach, molecules with an acid (COOH) group on each end are reacted with molecules containing amine (NH2) groups on each end. The resulting nylon is named on the basis of the number of carbon atoms separating the two acid groups and the two amines. These are formed into monomers of intermediate molecular weight, which are then reacted to form long polymer chains.

Solid nylon is used for mechanical parts such as machine screws, gears and other low- to medium-stress components previously cast in metal. Engineering-grade nylon is processed by extrusion, casting, and injection molding. Solid nylon is used in hair combs. Type 6/6 Nylon 101 is the most common commercial grade of nylon, and Nylon 6 is the most common commercial grade of molded nylon. Nylon is available in glass-filled variants which increase structural and impact strength and rigidity, and molybdenum sulfide-filled variants which increase lubricity.

Aramids are another type of polyamide with quite different chain structures which include aromatic groups in the main chain. Such polymers make excellent ballistic fibers.

Nylons are condensation copolymers formed by reacting equal parts of a diamine and a dicarboxylic acid, so that peptide bonds form at both ends of each monomer in a process analogous to polypeptide biopolymers. The numerical suffix specifies the numbers of carbons donated by the monomers; the diamine first and the diacid second. The most common variant is nylon 6-6 which refers to the fact that the diamine (hexamethylene diamine) and the diacid (adipic acid) each donate 6 carbons to the polymer chain. As with other regular copolymers like polyesters and polyurethanes, the "repeating unit" consists of one of each monomer, so that they alternate in the chain. Since each monomer in this copolymer has the same reactive group on both ends, the direction of the amide bond reverses between each monomer, unlike natural polyamide proteins which have overall directionality. In the laboratory, nylon 6-6 can also be made using adipoyl chloride instead of adipic. It is difficult to get the proportions exactly correct, and deviations can lead to chain termination at molecular weights less than a desirable 10,000 daltons. To overcome this problem, a crystalline, solid "nylon salt" can be formed at room temperature, using an exact 1:1 ratio of the acid and the base to neutralize each other. Heated to 285° C., the salt reacts to form nylon polymer. Above 20,000 daltons, it is impossible to spin the chains into yarn, so to combat this some acetic acid is added to react with a free amine end group during polymer elongation to limit the molecular weight. In practice, and especially for 6,6, the monomers are often combined in a water solution. The water used to make the solution is evaporated under controlled conditions, and the increasing concentration of "salt" is polymerized to the final molecular weight.

Homopolymer nylon 6, or polycaprolactam, is not a condensation polymer, but formed by a ring-opening polymerization (alternatively made by polymerizing aminocaproic acid). The peptide bond within the caprolactam is broken with the exposed active groups on each side being incorporated into two new bonds as the monomer becomes part of the polymer backbone. In this case, all amide bonds lie in the same direction, but the properties of nylon 6 are sometimes indistinguishable from those of nylon 6,6—except for melt temperature (N6 is lower) and some fiber properties in products like carpets and textiles. There is also nylon 9.

Nylon 5,10, made from pentamethylene diamine and sebacic acid has superior properties, but is more expensive to make. In keeping with this naming convention, "nylon 6,12" (N-6,12) or "PA-6,12" is a copolymer of a 6C diamine and a 12C diacid. Similarly for N-5,10 N-6,11; N-10,12, etc. Other nylons include copolymerized dicarboxylic acid/diamine products that are not based upon the monomers listed above. For example, some aromatic nylons are polymerized with the addition of diacids like terephthalic acid (Kevlar) or isophthalic acid (Nomex), more commonly associated with polyesters. There are copolymers of N-6,6/N6; copolymers of N-6,6/N-6/N-12; and others. Because of the way polyamides are formed, nylon would seem to be limited to unbranched, straight chains. But "star" branched nylon can be produced by the condensation of dicarboxylic acids with polyamines having three or more amino groups.

Above their melting temperatures, Tm, thermoplastics like nylon are amorphous solids or viscous fluids in which the chains approximate random coils. Below Tm, amorphous regions alternate with regions which are lamellar crystals. The amorphous regions contribute elasticity and the crystalline regions contribute strength and rigidity. The planar amide (—CO—NH—) groups are very polar, so nylon forms multiple hydrogen bonds among adjacent strands. Because the nylon backbone is so regular and symmetrical, especially if all the amide bonds are in the trans configuration, nylons often have high crystallinity and make excellent fibers. The amount of crystallinity depends on the details of formation, as well as on the kind of nylon. Apparently it can never be quenched from a melt as a completely amorphous solid.

Nylon 6,6 can have multiple parallel strands aligned with their neighboring peptide bonds at coordinated separations of exactly 6 and 4 carbons for considerable lengths, so the carbonyl oxygens and amide hydrogens can line up to form interchain hydrogen bonds repeatedly, without interruption. Nylon 5,10 can have coordinated runs of 5 and 8 carbons. Thus parallel (but not antiparallel) strands can participate in extended, unbroken, multi-chain ß-pleated sheets, a strong and tough supermolecular structure similar to that found in natural silk fibroin and the ß-keratins in feathers. (Proteins have only an amino acid α-carbon separating sequential —CO—NH— groups.) Nylon 6 will form uninterrupted H-bonded sheets with mixed directionalities, but the ß-sheet wrinkling is somewhat different. The three-dimensional disposition of each alkane hydrocarbon chain depends on rotations about the 109.47° tetrahedral bonds of singly-bonded carbon atoms.

Block nylon tends to be less crystalline, except near the surfaces due to shearing stresses during formation. Nylon is clear and colorless, or milky, but is easily dyed. Multistranded nylon cord and rope is slippery and tends to unravel. The ends can be melted and fused with a heat source such as a flame or electrode to prevent this.

When dry, polyamide is a good electrical insulator. However, polyamide is hygroscopic. The absorption of water will change some of the material's properties such as its electrical resistance. Nylon is less absorbent than wool or cotton.

Nylon can be used as the matrix material in composite materials, with reinforcing fibers like glass or carbon fiber, and has a higher density than pure nylon. Such thermoplastic composites (25% glass fiber) are frequently used in car components next to the engine, such as intake manifolds, where the good heat resistance of such materials makes them feasible competitors to metals.

All nylons are susceptible to hydrolysis, especially by strong acids, a reaction essentially the reverse of the synthetic reaction shown above. The molecular weight of nylon products so attacked drops fast, and cracks form quickly at the affected zones. Lower members of the nylons (such as nylon 6) are affected more than higher members such as nylon 12. This means that nylon parts cannot be used in contact with sulfuric acid for example, such as the electrolyte used in lead-acid batteries. When being molded, nylon must be dried to prevent hydrolysis in the molding machine barrel since water at high temperatures can also degrade the polymer.

Polyimide (PI)

Polyimide is a polymer of imide monomers. Thermosetting polyimides are commercially available as uncured resins, stock shapes, thin sheets, laminates and machines parts. Thermoplastic polyimides are very often called pseudothermoplastic. There are two general types of polyimides. One type, so-called linear polyimides, is made by combining imides into long chains. Aromatic heterocyclic polyimides are the other usual kind. Examples of polyimide films include Apical, Kapton, UPILEX, VTEC PI, Norton TH and Kaptrex. Polyimide parts and shapes include VTEC PI, Meldin, Vespel and typical monomers include pyromellitic dianhydride and 4,4'-oxydianiline.

Thermosetting polyimides are known for thermal stability, good chemical resistance, excellent mechanical properties, and characteristic orange/yellow color. Polyimides compounded with graphite or glass fiber reinforcements have flexural strengths of up to 50,000 psi and flexural moduli of 3,000,000 psi. Thermoset polyimides exhibit very low creep and high tensile strength. These properties are maintained during continuous use to temperatures of 232° C. and for short excursions, as high as 482° C. Molded polyimide parts and laminates have very good heat resistance. Normal operating temperatures for such parts and laminates range from cryogenic to those exceeding 260° C. Polyimides are also inherently resistant to flame combustion and do not usually need to be mixed with flame retardants. Most carry a UL rating of VTM-0. Polyimide laminates have a flexural strength half life at 249° C. of 400 hours.

Typical polyimide parts are not affected by commonly used solvents and oils including hydrocarbons, esters, ethers, alcohols and freons. They also resist weak acids but are not recommended for use in environments that contain alkalis or inorganic acids. Some polyimides, such as CP1 and CORIN XLS, are solvent-soluble and exhibit high optical clarity. The solubility properties lend them towards spray and low temperature cure applications.

The polyimide materials are lightweight, flexible, resistant to heat and chemicals. Therefore, they are used in the electronics industry for flexible cables, as an insulating film on magnet wire and for medical tubing. For example, in a laptop computer, the cable that connects the main logic board to the display (which must flex every time the laptop is opened or closed) is often a polyimide base with copper conductors. The semiconductor industry uses polyimide as a high-temperature adhesive; it is also used as a mechanical stress buffer. Some polyimide can be used like a photoresist; both "positive" and "negative" types of photoresist-like polyimide exist in the market.

Thermoset film polyimide has the following properties: Density 1.40-1.67 g/cc; Water Absorption 1.40-3.00%; Moisture Absorption at Equilibrium 0.400-1.80%; Water Absorption at Saturation 1.20-2.50%; Moisture Vapor Transmission 2.40-17.5 cc-mm/mg-24 hr-atm; Oxygen Transmission 9.90 cc-mm/mg-24 hr-atm; Thickness 22.0-187 microns; Film Tensile Strength at Yield, MD 49.0-255 MPa; Film Tensile Strength at Yield, TD 100-160 MPa; Film Elongation at Break, MD 10.0-85.0%; Film Elongation at Yield, MD 40.0-50.0%; Film Elongation at Yield, TD 45.0-55.0%; Tensile Strength, Yield 73.3-160 MPa; Elongation at Yield 10.0-45.0%; Poissons Ratio 0.340; Secant Modulus 2.28-5.20 GPa; Secant Modulus, MD 1.76-9.12 GPa; Impact Test 0.686-1.56 J; Coefficient of Friction 0.400-0.480; Coefficient of Friction, Static 0.630; Tear Strength Test 7.20-430; Peel Strength 0.240 kN/m; Elmendorf Tear Strength MD 8.20-270 g; Film Tensile Strength at Break, MD 98.1-736 MPa; Electrical Resistivity 1.00e+10-2.30e+17 ohm-cm; 1.00e+15-1.00e+16 ohm-cm @Temperature 200° C.; Surface Resistance 10000-1.00e+17 ohm; 1.00e+15-1.00e+15 ohm @Temperature 200° C.; Dielectric Constant 2.70-4.00; Dielectric Strength 48.0-272 kV/mm @Temperature 200° C.; Dissipation Factor 0.00130-0.0100; CTE, linear 12.0-20.0 µm/m-° C.; 32.0-40.0 µm/m-° C. @Temperature 100-300° C.; Specific Heat Capacity 1.09-1.13 J/g-° C.; Thermal Conductivity 0.120-0.289 W/m-K; Maximum Service Temperature, Air 180-400° C.; Minimum Service Temperature, Air −269° C.; Glass Temperature 360-500° C.; Oxygen Index 37.0-66.0%; Shrinkage 0.0100-0.200%; Refractive Index 1.70.

Liquid Crystal Polymer (LCP)

Liquid-crystal polymers (LCPs) are a class of aromatic polyester polymers. They are extremely unreactive and inert, and highly resistant to fire. Liquid crystallinity in polymers may occur either by dissolving a polymer in a solvent (lyotropic liquid-crystal polymers) or by heating a polymer above its glass or melting transition point (thermotropic liquid-crystal polymers). Liquid-crystal polymers are present in melted/liquid or solid form. In liquid form liquid-crystal polymers have primarily applications in liquid-crystal displays (LCDs). In solid form the main example of lyotropic LCPs is the commercial aramid known as Kevlar. The chemical structure of this aramid consists of linearly substituted aromatic rings linked by amide groups. In a similar way, several series of thermotropic LCPs have been commercially produced by several companies (e.g., Vectra). A high number of LCPs, produced in the 1980s, displayed order in the melt phase analogous to that exhibited by nonpolymeric liquid crystals. Processing of LCPs from liquid-crystal phases (or mesophases) gives rise to fibers and injected materials having high mechanical properties as a consequence of the self-reinforcing properties derived from the macromolecular orientation in the mesophase. Today, LCPs can be melt-processed on conventional equipment at high speeds with excellent replication of mold details.

A unique class of partially crystalline aromatic polyesters based on p-hydroxybenzoic acid and related monomers, liquid-crystal polymers is capable of forming regions of highly ordered structure while in the liquid phase. However, the degree of order is somewhat less than that of a regular solid crystal. Typically LCPs have a high mechanical strength at high temperatures, extreme chemical resistance, inherent flame retardancy, and good weatherability. Liquid-crystal polymers come in a variety of forms from sinterable high temperature to injection moldable compounds. LCP can be welded, though the lines created by welding are a weak point in the resulting product. LCP has a high Z-axis coefficient of thermal expansion.

LCPs are exceptionally inert. They resist stress cracking in the presence of most chemicals at elevated temperatures, including aromatic or halogenated hydrocarbons, strong acids, bases, ketones, and other aggressive industrial substances. Hydrolytic stability in boiling water is excellent. Environments that deteriorate the polymers are high-temperature steam, concentrated sulfuric acid, and boiling caustic materials. Because of their various properties, LCPs are useful for electrical and mechanical parts, food containers, and any other applications requiring chemical inertness and high strength.

High-Density Polyethylene (HDPE)

High-density polyethylene (HDPE) or polyethylene high-density (PEHD) is a polyethylene thermoplastic made from petroleum. HDPE has little branching, giving it stronger intermolecular forces and tensile strength than lower-density polyethylene. It is also harder and more opaque and can withstand somewhat higher temperatures (120° C. for short periods, 110° C. continuously). High-density polyethylene, unlike polypropylene, cannot withstand normally-required autoclaving conditions. The lack of branching is ensured by an appropriate choice of catalyst (e.g., Ziegler-Natta catalysts) and reaction conditions. HDPE contains the chemical elements carbon and hydrogen. Hollow goods manufactured through blow molding are the most common application area for HDPE.

Polypropylene (PP)

Polypropylene or polypropene (PP) is a thermoplastic polymer, made by the chemical industry and used in a wide variety of applications, including packaging, textiles (e.g. ropes, thermal underwear and carpets), stationery, plastic parts and reusable containers of various types, laboratory equipment, loudspeakers, automotive components, and polymer banknotes. An addition polymer made from the monomer propylene, it is rugged and unusually resistant to many chemical solvents, bases and acids.

Most commercial polypropylene is isotactic and has an intermediate level of crystallinity between that of low density polyethylene (LDPE) and high density polyethylene (HDPE); its Young's modulus is also intermediate. PP is normally tough and flexible, especially when copolymerized with ethylene. This allows polypropylene to be used as an engineering plastic, competing with materials such as ABS. Polypropylene is reasonably economical, and can be made translucent when uncolored but is not as readily made transparent as polystyrene, acrylic or certain other plastics. It is often opaque and/or colored using pigments. Polypropylene has good resistance to fatigue.

Polypropylene has a melting point of ~160° C. (320° F.), as determined by Differential scanning calorimetry (DSC). The MFR (Melt Flow Rate) or MFI (Melt Flow Index) is a measure of PP's molecular weight. This helps to determine how easily the molten raw material will flow during processing. Higher MFR PPs fill the plastic mold more easily during the injection or blow molding production process. As the melt flow increases, however, some physical properties, like impact strength, will decrease.

There are three general types of PP: homopolymer, random copolymer and block copolymer. The comonomer used is typically ethylene. Ethylene-propylene rubber or EPDM added to PP homopolymer increases its low temperature impact strength. Randomly polymerized ethylene monomer added to PP homopolymer decreases the polymer crystallinity and makes the polymer more transparent.

Polypropylene is liable to chain degradation from exposure to UV radiation such as that present in sunlight. For external applications, UV-absorbing additives must be used. Carbon black also provides some protection from UV attack. The polymer can also be oxidized at high temperatures, a common problem during molding operations. Anti-oxidants are normally added to prevent polymer degradation.

The relative orientation of each methyl group (CH3 in the figure at left) relative to the methyl groups on neighboring monomers has a strong effect on the finished polymer's ability to form crystals, because each methyl group takes up space and constrains backbone bending.

Like most other vinyl polymers, useful polypropylene cannot be made by radical polymerization due to the higher reactivity of the allylic hydrogen (leading to dimerization) during polymerization. Moreover, the material that would result from such a process would have methyl groups arranged randomly, so called atactic PP. The lack of long-range order prevents any crystallinity in such a material, giving an amorphous material with very little strength and only specialized qualities suitable for niche end uses.

A Ziegler-Natta catalyst is able to limit incoming monomers to a specific orientation, only adding them to the polymer chain if they face the right direction. Most commercially available polypropylene is made with such Ziegler-Natta catalysts, which produce mostly isotactic polypropylene (the upper chain in the figure above). With the methyl group consistently on one side, such molecules tend to coil into a helical shape; these helices then line up next to one another to form the crystals that give commercial polypropylene many of its desirable properties.

More precisely engineered Kaminsky catalysts have been made, which offer a much greater level of control. Based on metallocene molecules, these catalysts use organic groups to control the monomers being added, so that a proper choice of catalyst can produce isotactic, syndiotactic, or atactic polypropylene, or even a combination of these. Aside from this qualitative control, they allow better quantitative control, with a much greater ratio of the desired tacticity than previous Ziegler-Natta techniques. They also produce narrower molecular weight distributions than traditional Ziegler-Natta catalysts, which can further improve properties.

To produce a rubbery polypropylene, a catalyst can be made which yields isotactic polypropylene, but with the organic groups that influence tacticity held in place by a relatively weak bond. After the catalyst has produced a short length of polymer which is capable of crystallization, light of the proper frequency is used to break this weak bond, and remove the selectivity of the catalyst so that the remaining length of the chain is atactic. The result is a mostly amorphous material with small crystals embedded in it. Since each chain has one end in a crystal but most of its length in the soft, amorphous bulk, the crystalline regions serve the same purpose as vulcanization.

Melt processing of polypropylene can be achieved via extrusion and molding. Common extrusion methods include production of melt blown and spun bond fibers to form long rolls for future conversion into a wide range of useful products such as face masks, filters, nappies and wipes. The most common shaping technique is injection molding, which is used for parts such as cups, cutlery, vials, caps, containers, housewares and automotive parts such as batteries. The related techniques of blow molding and injection-stretch blow molding are also used, which involve both extrusion and molding.

The large number of end use applications for PP is often possible because of the ability to tailor grades with specific molecular properties and additives during its manufacture. For example, antistatic additives can be added to help PP surfaces resist dust and dirt. Many physical finishing techniques can also be used on PP, such as machining. Surface treatments can be applied to PP parts in order to promote adhesion of printing ink and paints.

Since polypropylene is resistant to fatigue, most plastic living hinges, such as those on flip-top bottles, are made from this material. However, it is important to ensure that chain molecules are oriented across the hinge to maximize strength. Very thin sheets of polypropylene are used as a dielectric within certain high performance pulse and low loss RF capacitors.

High-purity piping systems are built using polypropylene. Stronger, more rigid piping systems, intended for use in potable plumbing, hydronic heating and cooling, and reclaimed water applications, are also manufactured using polypropylene. This material is often chosen for its resistance to corrosion and chemical leaching, its resilience against most forms of physical damage, including impact and freezing, and its ability to be joined by heat fusion rather than gluing.

Many plastic items for medical or laboratory use can be made from polypropylene because it can withstand the heat in an autoclave. Its heat resistance also enables it to be used as the manufacturing material of consumer-grade kettles. Food containers made from it will not melt in the dishwasher, and do not melt during industrial hot filling processes. For this reason, most plastic tubs for dairy products are polypropylene sealed with aluminum foil (both heat-resistant materials). After the product has cooled, the tubs are often given lids made of a less heat-resistant material, such as LDPE or polystyrene. Such containers provide a good hands-on example of the difference in modulus, since the rubbery (softer, more flexible) feeling of LDPE with respect to PP of the same thickness is readily apparent. Rugged, translucent, reusable plastic containers made in a wide variety of shapes and sizes for consumers from various companies such as Rubbermaid and Sterilite are commonly made of polypropylene, although the lids are often made of somewhat more flexible LDPE so they can snap on to the container to close it. Polypropylene can also be made into disposable bottles to contain liquid, powdered or similar consumer products, although HDPE and polyethylene terephthalate are commonly also used to make bottles. Plastic pails, car batteries, wastebaskets, cooler containers, dishes and pitchers are often made of polypropylene or HDPE, both of which commonly have rather similar appearance, feel, and properties at ambient temperature.

Polypropylene is a major polymer used in nonwovens, with over 50% used for diapers or sanitary products where it is treated to absorb water (hydrophilic) rather than naturally repelling water (hydrophobic). Other interesting non woven uses include filters for air, gas and liquids where the fibers can be formed into sheets or webs that can be pleated to form cartridges or layers that filter in various efficiencies in the 0.5 to 30 micron range. Such applications could be seen in the house as water filters or air conditioning type filters. The high surface area and naturally hydrophobic polypropylene nonwovens are ideal absorbers of oil spills with the familiar floating barriers near oil spills on rivers.

A common application for polypropylene is as Biaxially Oriented polypropylene (BOPP). These BOPP sheets are used to make a wide variety of materials including clear bags. When polypropylene is biaxially oriented, it becomes crystal clear and serves as an excellent packaging material for artistic and retail products.

Polypropylene's most common medical use is in the synthetic, nonabsorbable suture Prolene, manufactured by Ethicon Inc.

Polypropylene is most commonly used for plastic moldings where it is injected into a mold while molten, forming complex shapes at relatively low cost and high volume, examples include bottle tops, bottles and fittings.

Recently it has been produced in sheet form and this has been widely used for the production of stationary folders, packaging and storage boxes. The wide color range, durability and resistance to dirt make it ideal as a protective cover for papers and other materials. It is used in Rubik's cube stickers because of these characteristics.

Expanded Polypropylene (EPP) is a foam form of polypropylene. EPP has very good impact characteristics due to its low stiffness; this allows EPP to resume its shape after impacts. EPP is extensively used in model aircraft and other radio controlled vehicles by hobbyists. This is mainly due to its ability to absorb impacts, making this an ideal material for RC aircraft for beginners and amateurs.

Silicon Dioxide ($SiO_2$)

The chemical compound silicon dioxide, also known as silica, is an oxide of silicon with a chemical formula of $SiO_2$. Oxides of silicon, commonly referred to as "SiOx", include silicon dioxide. Silica is most commonly found in nature as sand or quartz, as well as in the cell walls of diatoms. It is a principal component of most types of glass and substances such as concrete. Silica is the most abundant mineral in the Earth's crust.

$SiO_2$ has a number of distinct crystalline forms in addition to amorphous forms. With the exception of stishovite and fibrous silica, all of the crystalline forms involve tetrahedral $SiO_4$ units linked together by shared vertices in different arrangements. Silicon-oxygen bond lengths vary between the different crystal forms. In a-quartz the Si—O—Si angle is 144°. The only stable form under normal conditions is a-quartz and this is the form in which crystalline silicon dioxide is usually encountered.

Silicon dioxide is formed when silicon is exposed to oxygen (or air). A very thin layer (approximately 1 nm or 10 Å) of so-called 'native oxide' is formed on the surface when silicon is exposed to air under ambient conditions. Higher temperatures and alternative environments are used to grow well-controlled layers of silicon dioxide on silicon, for example at temperatures between 600 and 1200° C., using the so-called "dry" or "wet" oxidation with $O_2$ or $H_2O$, respectively. The thickness of the layer of silicon replaced by the dioxide is 44% of the thickness of the silicon dioxide layer produced. Alternative methods used to deposit a layer of $SiO_2$ include: Low temperature oxidation (400-450° C.) of silane; Decomposition of tetraethyl orthosilicate (TEOS) at 680-730° C.; Plasma enhanced chemical vapor deposition using TEOS at about 400° C.; Polymerization of tetraethyl orthosilicate (TEOS) at below 100° C. using amino acid as catalyst.

Pyrogenic silica (sometimes called fumed silica or silica fume), which is a very fine particulate form of silicon dioxide, is prepared by burning $SiCl_4$ in an oxygen rich hydrocarbon flame to produce a "smoke" of $SiO_2$. Amorphous silica, silica gel, is produced by the acidification of solutions of sodium silicate to produce a gelatinous precipitate that is then washed and then dehydrated to produce colorless microporous silica.

Aluminum Oxide ($Al_2O_3$)

Aluminum oxide is an amphoteric oxide of aluminum with the chemical formula $Al_2O_3$. It is also commonly referred to as alumina, corundum, sapphire, ruby or aloxite. Aluminum oxide is an electrical insulator but has a relatively high thermal conductivity (40 $Wm^{-1}K^{-1}$) for a ceramic material. In its most commonly occurring crystalline form, called corundum or α-aluminum oxide, its hardness makes it suitable for use as an abrasive and as a component in cutting tools. Aluminum oxide is responsible for resistance of metallic aluminum to weathering. Metallic aluminum is very reactive with atmospheric oxygen, and a thin passivation layer of alumina (4 nm thickness) forms in about 100 picoseconds on any exposed aluminum surface. This layer protects the metal from further oxidation. The thickness and properties of this oxide layer can be enhanced using a process called anodizing. A number of alloys, such as aluminum bronzes, exploit this property by including a proportion of aluminum in the alloy to enhance corrosion resistance. The alumina generated by anodizing is typically amorphous, but discharge assisted oxidation processes such as plasma electrolytic oxidation result in a significant proportion of crystalline alumina in the coating, enhancing its hardness. The most common form of crystalline alumina, a-aluminum oxide, is known as corundum. Alumina also exists in other phases. Each has a unique crystal structure and properties. Aluminum hydroxide minerals are the main component of bauxite, the principal ore of aluminum. Alumina tends to be multi-phase; e.g., constituting several of the alumina phases rather than solely corundum.

Polyvinyl Alcohol (PVOH, PVA, or PVAL)

Polyvinyl alcohol (PVOH, PVA, or PVAL) is a water-soluble synthetic polymer. Polyvinyl alcohol has excellent film forming, emulsifying, and adhesive properties. It is also resistant to oil, grease and solvent. It is odorless and non-toxic. It has high tensile strength and flexibility, as well as high oxygen and aroma barrier properties. However these properties are dependent on humidity, in other words, with higher humidity more water is absorbed. The water, which acts as a plasticizer, will then reduce its tensile strength, but increase its elongation and tear strength. PVA is fully degradable and is a quick dissolver. PVA has a melting point of 230° C. and 180-190° C. for the fully hydrolyzed and partially hydrolyzed grades, respectively. It decomposes rapidly above 200° C. as it can undergo pyrolysis at high temperatures.

PVA is an atactic material but exhibits crystallinity as the hydroxyl groups are small enough to fit into the lattice without disrupting it. Unlike most vinyl polymers, PVA is not prepared by polymerization of the corresponding monomer. The monomer, vinyl alcohol, almost exclusively exists as the tautomeric form, acetaldehyde. PVA instead is prepared by partial or complete hydrolysis of polyvinyl acetate to remove acetate groups.

Nanopolymers

Polymer nanocomposite (PNC) is a polymer or copolymer having dispersed in its nanoparticles. These may be of different shape (e.g., platelets, fibers, spheroids), but at least one dimension is in the range of 1 to 50 nm. The transition from micro- to nano-particles leads to changes in physical as well as chemical properties. Two of the major factors in this are the increase in the ratio of the surface area to volume, and the size of the particle. The increase in surface area-to-volume ratio, which increases as the particles get smaller, leads to an increasing dominance of the behavior of atoms on the surface area of particle over that of those interior of the particle. This affects the properties of the particles when they are reacting with other particles. Because of the higher surface area of the nano-particles the interaction with the other particles within the mixture is more and this increases the strength, heat resistance etc and many factors do change for the mixture.

An example of a nanopolymer is silicon nanospheres which show quite different characteristics. The particle size is 40-100 nm and it is much harder than silicon (a hardness between that of sapphire and diamond). Many technical applications of biological objects like proteins, viruses or bacteria such as chromatography, optical information technology, sensors, catalysis and drug delivery require their immobilization. Carbon nanotubes, gold particles and synthetic polymers are used for this purpose. This immobilization has been achieved predominantly by adsorption or by chemical binding and to a lesser extent by incorporating these objects as guests in host matrices. In the guest host systems, an ideal method for the immobilization of biological objects and their integration into hierarchical architectures should be structured on a nanoscale to facilitate the interactions of biological nano-objects with their environment. Due to the large number of natural or synthetic polymers available and the advanced techniques developed to process such systems to nanofibers, rods, tubes etc make polymers a good platform for the immobilization of biological objects.

Polymer fibers are, in general, produced on a technical scale by extrusion, e.g., a polymer melt or a polymer solution is pumped through cylindrical dies and spun/drawn by a take-up device. The resulting fibers have diameters typically on the 10-μm scale or above. To come down in diameter into the range of several hundreds of nanometers or even down to a few nanometers, electrospinning is today still the leading polymer processing technique available. A strong electric field of the order of 103 V/cm is applied to the polymer solution droplets emerging from a cylindrical die. The electric charges, which are accumulated on the surface of the droplet, cause droplet deformation along the field direction, even though the surface tension counteracts droplet evolution. In supercritical electric fields, the field strength overbears the surface tension and a fluid jet emanates from the droplet tip. The jet is accelerated towards the counter electrode. During this transport phase, the jet is subjected to strong electrically driven circular bending motions that cause a strong elongation and thinning of the jet, a solvent evaporation until, finally, the solid nanofiber is deposited on the counter electrode.

Electro spinning, co-electrospinning, and the template methods based on nanofibers yield nano-objects which are, in principle, infinitively long. For a broad range of applications including catalysis, tissue engineering, and surface modification of implants this infinite length is an advantage. But in some applications like inhalation therapy or systemic drug delivery, a well-defined length is required. The template method to be described in the following has the advantage such that it allows the preparation of nanotubes and nanorods with very high precision. The method is based on the use of well defined porous templates, such as porous aluminum or silicon. The basic concept of this method is to exploit wetting processes. A polymer melt or solution is brought into contact with the pores located in materials characterized by high energy surfaces such as aluminum or silicon. Wetting sets in and covers the walls of the pores with a thin film with a thickness of the order of a few tens of nanometers. This process happens typically within a minute for temperatures about 50 K above the melting temperature or glass transition temperature, even for highly viscous polymers, such as, for instance, polytetrafluoroethylene, and this holds even for pores with an aspect ratio as large as 10,000. To obtain nanotubes, the polymer/template system is cooled down to room temperature or the solvent is evaporated, yielding pores covered with solid layers. The resulting tubes can be removed by mechanical forces for tubes up to 10 μm in length, e.g., by just drawing them out from the pores or by selectively dissolving the template. The diameter of the nanotubes, the distribution of the diameter, the homogeneity along the tubes, and the lengths can be controlled.

The size-dependent and pressure-dependent glass transition temperatures of free-standing films or supported films having weak interactions with substrates decreases with decreasing of pressure and size. However, the glass transition temperature of supported films having strong interaction with substrates increases of pressure and the decrease of size.

Nanocomposites are polymer structures that contain fillers, typically silicate nanoclays, with at least one dimension in the nanometer range. The fillers separate into tiny platelets that disperse into a matrix of layers. Because the matrix of layers creates a tortuous path for gasses trying to permeate through the film, the barrier properties of the modified polymer are improved. However, the challenge is to ensure that that the filler dispersion is consistent. In addition to better barrier properties, nanocomposites modified films also have improved dimensional stability and stiffness and, because crystallinity is increased, enhanced clarity. Nanocomposite masterbatches are commercially available for nylon and polyolefins. The oxygen barrier of nylon nanocomposite films can be as much as 50 percent higher than a nonmodified nylon. Polyethylene and polypropylene nanocomposite structures have shown improvement in gas barrier of 25 to 50 percent and in water vapor of 10 to 15 percent in laboratory settings. Achieving consistent barrier properties on a commercial scale remains challenging. Nanocomposite technology is very much an emerging science. It shows a great deal of promise and as more options become available for film applications it will have a significant impact on barrier material options.

Saran

Saran is the trade name for a number of polymers made from vinylidene chloride (especially polyvinylidene chloride or PVDC), along with other monomers. Saran film has a very low permeability to water vapor, flavor and aroma molecules, and oxygen compared to other plastics. The barrier to oxygen prevents food spoilage, and the barrier to flavor and aroma molecules helps food retain its flavor and aroma. Saran also possesses $CO_2$ barrier properties.

Polytrimethylene Terephthalate (PTT)

Polytrimethylene Terephthalate (PTT) is a semicrystalline polymer that has many of the same advantages as PET. PTT exhibits good tensile strength, flexural strength, and stiffness. It has excellent flow and surface finish. PTT can have more uniform shrinkage and better dimensional stability in some applications than competing semicrystalline materials. PTT has excellent resistance to a broad range of chemicals at room temperature, including aliphatic hydrocarbons, gasoline, carbon tetrachloride, perchloroethylene, oils, fats, alcohols, glycols, esters, ethers and dilute acids and bases. Strong bases may attack PTT compounds. Impact modifiers and reinforcing fibers (long glass, short glass, or carbon) can be used to increase the impact properties, as well as the strength and stiffness of PTT.

Polytrimethylene Naphthalate (PTN)

Poly(trimethylene phthalates or naphthalate) and copolymers are aromatic polyesters made by polycondensation of 1,3-propanediol (PDO) and terephthalic acid (PTT), isophthalic acid (PTI) or naphthalic acid (PTN) and/or with comonomers (isophthalic acid, 1,4-butanediol, etc.). Films of PTN possess good barrier properties.

Polyethylene Naphthalate (PEN)

Polyethylene naphthalate (PEN) is a polyester with good barrier properties (even better than polyethylene terephthalate). Because it provides a very good oxygen barrier, it is particularly well-suited for bottling beverages that are susceptible to oxidation, such as beer. It is prepared from ethylene glycol and one or more naphthalene dicarboxylic acids by condensation polymerization.

Polyurethane

A polyurethane is any polymer consisting of a chain of organic units joined by urethane (carbamate) links. Polyurethane polymers are formed through step-growth polymerization by reacting a monomer containing at least two isocyanate functional groups with another monomer containing at least two hydroxyl (alcohol) groups in the presence of a catalyst. Polyurethane formulations cover an extremely wide range of stiffness, hardness, and densities. Though the properties of the polyurethane are determined mainly by the choice of polyol, the diisocyanate exerts some influence, and must be suited to the application. The cure rate is influenced by the functional group reactivity and the number of functional isocyanate groups. The mechanical properties are influenced by the functionality and the molecular shape. The choice of diisocyanate also affects the stability of the polyurethane upon exposure to light. Polyurethanes made with aromatic diisocyanates yellow with exposure to light, whereas those made with aliphatic diisocyanates are stable. Softer, elastic, and more flexible polyurethanes result when linear difunctional polyethylene glycol segments, commonly called polyether polyols, are used to create the urethane links. This strategy is used to make spandex elastomeric fibers and soft rubber parts, as well as foam rubber. More rigid products result if polyfunctional polyols are used, as these create a three-dimensional cross-linked structure which, again, can be in the form of a low-density foam.

Polyether Block Amide (Pebax®)

Polyether block amide is a thermoplastic elastomer or a flexible polyamide without plasticizer consisting of a regular linear chain of rigid polyamide segments and flexible polyether segments.

Parylene C

Parylene is the tradename for a variety of chemical vapor deposited poly(p-xylylene) polymers used as moisture barriers and electrical insulators. Among them, Parylene C is the most popular due to its combination of barrier properties, cost, and other manufacturing advantages.

Silicone

Silicones, also referred to as polymerized siloxanes or polysiloxanes, are mixed inorganic-organic polymers with the chemical formula $[R_2SiO]_n$, where R is an organic group such as methyl, ethyl, or phenyl. These materials consist of an inorganic silicon-oxygen backbone ( . . . —Si—O—Si—O—Si—O— . . . ) with organic side groups attached to the silicon atoms, which are four-coordinate. In some cases organic side groups can be used to link two or more of these —Si—O— backbones together. By varying the —Si—O— chain lengths, side groups, and crosslinking, silicones can be synthesized with a wide variety of properties and compositions. They can vary in consistency from liquid to gel to rubber to hard plastic. The most common siloxane is linear polydimethylsiloxane (PDMS), a silicone oil. The second largest group of silicone materials is based on silicone resins, which are formed by branched and cage-like oligosiloxanes.

Fabrication of the Composite Wall

The various layers of the composite wall, including the $CO_2$ barrier layers, need not be situated in any particular order, but those of superior resistance to acidity, temperature, mechanical abrasion, and superior biocompatibility profile are preferably employed as layers contacting the gastric environment. Those with superior resistance to, e.g., acidity and temperature, are preferably employed as layers contacting the central lumen of the balloon.

The various layers of the wall can include a single layer or up to 10 or more different monolayers; however, a film thickness of from 0.001 inches (0.00254 cm) to 0.0025 inches (0.00635 cm) thick is desirable such that the resulting balloon compacted to fit into a swallowable capsule. The resulting composite wall preferably has good performance specifications with respect to each category listed in Table 1.

Films that are co-extruded are advantageously employed, as some adhesives may contain leachables that are undesirable from a biocompatibility perspective. In addition, coextrusion allows for better blending such that the materials maintain their original properties when combined in this fashion and are less likely to be subject to delamination when exposed to gastric motility forces.

Combining films with similar properties, e.g., two film layers with excellent $CO_2$ barrier properties, in a composite wall is advantageous for use in a gastric balloon containing $CO_2$ as the inflation gas. A primary advantage of such composite films is that restrictions on film thickness can be observed without sacrifice of $CO_2$ retention properties. Such a configuration also contributes to reducing the effects of processing damage (e.g., manufacturing and compacting) and damage due to exposure to in vivo conditions (e.g., gastric motility forces).

In a particularly preferred embodiment, the composite wall includes a plurality of layers. The first layer is an outer protective layer that is configured for exposure to the gastric environment. This layer is resistant to mechanical forces, exposure to water (vapor), abrasion, and high acidity levels. Polyethylene terephthalate is particularly preferred for the layer exposed to the gastric environment, and is especially resistant to water and humidity. The underside of the PET layer is provided with a coating of SiOx as a $CO_2$ barrier. The SiOx barrier is typically about 100 Å thick to about 800 Å thick, preferably about 200 Å to about 500 Å thick. SiOx layers that exceed 800 Å are found to be less advantageous; however, in certain embodiments they may be acceptable. A layer of EVOH sandwiched between two layers of LLDPE can be extrusion laminated, co-extruded, or adhesively bonded to the PET-SiOx layer. The EVOH layer is preferably at least 2 microns thick; however, in certain embodiments a thinner layer may be acceptable. Between the PET-SiOx layers and the EVOH layer is an adhesive layer, e.g., a dry polyurethane or polyurethane in solvent, or a low density polyethylene tie layer can be provided to increase the surface activity. Alternatively, corona treatment can be employed. Laminating or adhesive bonding can be employed to prepare a flat sheet composite wall. This preferred design is advantageous as the EVOH layer can compensate for $CO_2$ barrier properties lost in the SiOx application during processing; however, the EVOH layer may not be sufficient when used alone (without SiOx or another $CO_2$ barrier layer) since the EVOH layer loses $CO_2$ barrier properties due to water ingress and humidity. The EVOH and SiOx barrier layers are therefore complimentary to each other in maintaining a $CO_2$ loss of less than 40 cc/m²/day.

In a particularly preferred embodiment, the EVOH layer is sandwiched between layers of PE, so as to protect the EVOH layer from ambient water, humidity, or other conditions that can be detrimental to its structural integrity.

In an alternative embodiment, polyurethane is RF welded to saran to yield a 6-7 mil thick composite wall. In another embodiment, a five layer system is provided comprising a layer of saran sandwiched between two polyurethane layers. Between the saran layer and each of the polyurethane layers is a tie layer. The layers can be welded together or adhered using an adhesive. A representative example of material combinations that are commercially available or manufacturable is provided in Table 2. The orientation of the layers (innermost—in contact with the central balloon lumen, or outermost—in contact with the gastric environment) is also indicated if more than two layers are described to support a suggested composite wall.

Most of the film resins listed in Table 1 provide some degree of $CO_2$ barrier properties. Therefore, many can be used solely to form the balloon wall as a monolayer film; however they can also be used in conjunction with other film resins to meet the desired $CO_2$ maintenance specification for the useful life of the balloon. These film resins can also be coated with $CO_2$ barrier coatings listed in Table 1. Additional film layers can be added to form the total composite wall. While such additional layers may not impart substantial $CO_2$ barrier properties, they can provide structural and/or mechanical properties, protection for the other layers of the composite wall that are susceptible to water vapor, humidity, pH, or the like, or other desirable properties. The film layers can be assembled using various adhesives, via co-extrusion, via lamination, and/or using tie layers and such to create a composite wall that meets the requirements of an intragastric balloon suitable for use for at least 25 days, or up to 90 days or more, with the specified $CO_2$ retention properties. Table 2 provides a list of layers and layer combinations suitable for use in composite walls for an intragastric balloon. The composite description, resin abbreviation, configuration (single layer, bilayer, trilayer, or the like) and trade name of commercially available combinations are listed. The number of layers indicated does not include any adhesive layers or tie layers used to fabricate the composite wall, such that a 6-layer composite wall may, for example, have two or three adhesive layers and/or tie layers that make up the total composite wall, and therefore the total number of layers can be eight or nine in final form. The term "layer" as used herein is a broad term, and is to be given its ordinary and customary meaning to a person of ordinary skill in the art (and is not to be limited to a special or customized meaning), and refers without limitation to a single thickness of a homogenous substance (e.g., a coating such as SiOx, or a layer such as PET), as well as to a supporting layer having a coating thereon (wherein a "coating" is, e.g., a material typically employed in conjunction with substrate that provides structural support to the coating layer). For example, a PET-SiOx "layer" is referred to herein, wherein a layer of Si-Ox is provided on a supporting PET layer.

TABLE 2

| Example Film Composite Walls* | Abbreviation | Film Configuration | Trade name |
| --- | --- | --- | --- |
| polyethylene terephthalate | PET | Monolayer | Mylar |
| metalized oriented polyethylene terephthalate | metalized OPET | Bi-layer | |

TABLE 2-continued

| Example Film Composite Walls* | Abbreviation | Film Configuration | Trade name |
|---|---|---|---|
| polyvinyl alcohol coated oriented polypropylene | PVOH coated OPP | Bi-layer | Bicor |
| metallized biaxially oriented nylon 6 | metalized OPA6 | Bi-layer | |
| Biaxally oriented Nylon/ethylene vinyl alcohol/biaxally oriented Nylon | OPA/EVOH/OPA | trilayer | Honeywell Oxyshield Plus |
| Nylon/ethylene vinyl alcohol/Low Density Polyethylene | Nylon/EVOH/LDPE | trilayer | |
| polyvinylidene chloride coated oriented polyethylene terephthalate | PVDC/OPET | Bi-layer | Mylar |
| polyvinylidene chloride coated oriented polypropylene | PVCD/OPP | Bi-layer | |
| polyvinylidene chloride coated biaxally oriented Nylon 6 | PVCD/OPA6 | Bi-layer | Honeywell Oxyshield |
| high density polyethylene/ethylene vinyl alcohol | HDPE/EVOH | Bi-layer | |
| polypropylene/ethylene vinyl alcohol laminate | PP/EVOH | Bi-layer | |
| polyethylene terephthalate/ethylene vinyl alcohol | PET/EVOH | Bi-layer | |
| metallized oriented polypropylene | metalized OPP | Bi-layer | |
| sealable PVDC coated oriented polypropylene | PVDC coated PP | Bi-layer | |
| polyvinylidene fluoride | PVDF | Monolayer | |
| Polyvinyl chloride | PVC | Monolayer | |
| polyvinyl fluoride | PVF | Monolayer | Tedlar |
| polychlorofluoroethylene | PCTFE | Monolayer | ACLAR UltRx, SupRx, Rx |
| amine-based epoxy coated Nylon | epoxy coated PA6 | Bi-layer | Bairocade |
| polyvinyl chloride-polyvinylidene chloride copolymer | PVC-PVDC | Monolayer | |
| medium density polyethylene | MDPE | Monolayer | |
| Nylon/Polypropylene | Nylon/PP laminate | Bi-layer | |
| Nylon-High Density Polyethylene | Nylon-HDPE laminate | Bi-layer | |
| acetylene plasma coating on polyester | PET/A | Bi-layer | |
| difluoroethylene coating on polyethylene terephthalate | PET/DA | Bi-layer | |
| oriented polypropylene | OPP | Monolayer | |
| cast propylene | CPP | Monolayer | |
| high density polyethylene | HDPE | Monolayer | |
| cyclic olefin copolymer | COC | Monolayer | |
| oriented polystyrene | OPS | Monolayer | |
| Florinated Ethylene Propylene | FEP | Monolayer | |
| difluoroethylene coating on low density polyethylene | LDPE/D | Bi-layer | |
| difluoroethylene coating on polypropylene | PP/D | Bi-layer | |
| acetylene plasma coating on polypropylene | PP/A | Bi-layer | |
| acetylene plasma coating on low density polyethylene | LDPE/A | Bi-layer | |
| polybutylene terephthalate polyether glycol copolymer | TPC-ET | Monolayer | Hytrel |
| polyether block amide TPE | PEBA | Monolayer | Pebax |
| oxide coated biaxally oriented Nylon | oxide coated PA | Bi-layer | Honeywell Oxyshield Ultra |
| Nanoclay/nylon | MXD6/Nanoclay | Monolayer | Imperm/Aegis OXCE |
| Polyethylene Terephthalate/Silicone Dioxide | PET/SiOx | Monolayer | BestPET/ TechBarrier |
| Polyethylene Terephthalate/Oxygen scavengers | PET + 02 Scavengers | Monolayer | MonoxBar |
| Modified Polyethylene Terephthalate | Modified PET | Monolayer | DiamondClear |
| Polyethylene Terephthalate/Nylon 6 | PET/MXD6 | Bi-layer | HP867 |
| Amorphous polyvinyl alcohol | Amorphous PVOH | Monolayer | Nichigo G-Polymer |
| Nylon 6/Ethyl vinyl alcohol/Linear Low Density Polyethylene | Nylon 6/EVOH/LLDPE | Tri-layer | |
| Ethyl vinyl alcohol/Poly-Propylene/Ethyl vinyl alcohol | EVOH/PP/EVOH | Tri-layer | |
| Ethyl vinyl alcohol/Nylon | EVOH/Nylon | Bi-layer | |

TABLE 2-continued

| Example Film Composite Walls* | Abbreviation | Film Configuration | Trade name |
|---|---|---|---|
| Polyethylene/Ethyl vinyl alcohol/Polyethylene | PE/EVOH/PE | Tri-layer | |
| Polyethylene/Ethyl vinyl alcohol/Polyethylene Terephthalate | PE/EVOH/PET | Tri-layer | |
| Silicon dioxide-coated Polyethylene Terephthalate/Linear Low Density Polyethylene/Ethyl vinyl alcohol/Linear Low Density Polyethylene | PET-SiOx/LLDPE/EVOH/LLDPE | 5-layer | |
| Aluminum Oxide-coated Polyethylene Terephthalate/Polyethylene | PET-Al$_2$O$_3$/LLDPE | Tri-layer | |
| Polyethylene/Ethyl vinyl alcohol/Linear Low Density Polyethylene | PE/EVOH/LLDPE | Tri-layer | |
| Polyethylene Terephthalate/Polyethylene/Polyethylene/Bi-axially oriented Ethyl vinyl alcohol | PET/PE/OEVOH/PE | 4-layer | |
| Polyethylene Terephthalate/Polyethylene/Ethyl vinyl alcohol/Ethyl vinyl alcohol/Ethyl vinyl alcohol/Polyethylene | PET/PE/EVOH/EVOH/EVOH/PE | 6-layer | |
| Polyethylene Terephthalate/Polyethylene/Nylon 6/Ethyl vinyl alcohol/Nylon 6/Polyethylene | PET/PE/Nylon 6/EVOH/Nylon 6/PE | 6-layer | |
| Silicone dioxide-coated Polyethylene Terephthalate/Polyethylene/Ethyl vinyl alcohol/Polyethylene | PET-SiOx/PE/EVOH/PE | 4-layer | |
| Polyethylene/Ethyl vinyl alcohol/polyvinylchloride | PE/EVOH/PVDC | Tri-layer | |
| Polyethylene Terephthalate/Linear Low Density Polyethylene/Ethyl vinyl alcohol/Linear Low Density Polyethylene | PET/LLDPE/EVOH/LLDPE | 4-layer | |
| Kurrarister C-coated Polyethylene Terephthalate/Polyethylene/Ethyl vinyl alcohol/Polyethylene | PET-Kurrarister-C/PE/EVOH/PE | 5-layer | |
| Polyethylene Terephthalate/Polyethylene/Nylon 6/Ethyl vinyl alcohol/Nylon 6/Polyethylene | PET/PE/Nylon 6/EVOH/Nylon 6/PE | 6-layer | |
| Nylon 6/Ethyl vinyl alcohol/Polyvinylchloride/Low Density Polyethylene | Nylon 6/EVOH/PVDC/Nylon 6/LDPE | 5-layer | |
| Polyimide | PI | Monolayer | |
| Polyimide/Linear Low Density Polyethylene | PI/LLDPE | Bi-layer | |
| Polyimide/Polyvinylchloride | PI/PVdC | Bi-layer | |
| Polyimide/Polyvinylchloride/Linear Low Density Polyethylene | PI/PVdC/LLDPE | Bi-layer | |

*For all combinations where LLDPE, PE, HDPE, or LDPE is suggested, the polyethylene can alternatively be Low Density Polyethylene (LDPE), High Density Polyethylene (HDPE), or Linear Low Density Polyethylene (LLDPE). Particularly preferred is LLDPE.

In particularly preferred embodiments, the composite wall has a thickness of 0.0025 inches or less (2.5 mil or less); however, in certain embodiments a thicker composite wall may be acceptable. Generally it is preferred that the composite wall have a thickness of up to 0.002 inches (2 mil), or up to 0.0021 inches (2.1 mil).

Swallowable, Self-Inflating, Intragastric Balloon System

A swallowable, self-inflating intragastric balloon system according to selected preferred embodiments includes the following components: a balloon in a deflated and compacted state ("balloon"); an inner capsule or other container ("inner container") that contains one or more $CO_2$ generating components and that is present inside the lumen of the balloon; and an outer capsule, container, or coating ("outer container") that contains the balloon. The balloon further comprises a self-sealing valve system, preferably attached to the inner surface of the balloon by an adhesive or other means (e.g., welding), and an inoculation spacer to prevent puncture of the wall of the balloon and inner container by a needle or other means for injecting an liquid activation agent into the lumen of the balloon via the self-sealing valve. The outer container preferably incorporates the balloon in a compacted state (e.g., folded and rolled) with sufficient space to allow for activation liquid to be injected into the balloon. The liquid activation agent initiates separation, erosion, degradation, and/or dissolution of the inner container and generation of $CO_2$ upon contact with the inflation agent contained within the inner container, which subsequently causes outer container separation, erosion, degradation, and/or dissolution due to $CO_2$ gas pressure.

Figure 2A:
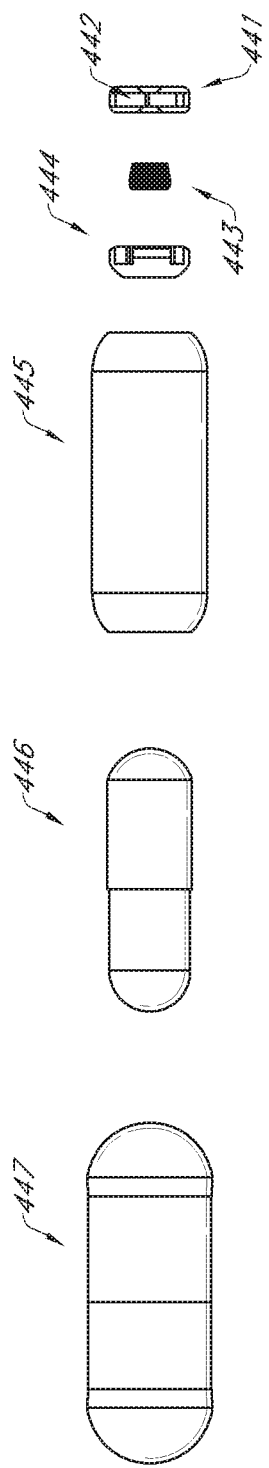
FIGS. 2A and 2B depict components of a swallowable, self-inflating intragastric balloon system.
Figure 2B:
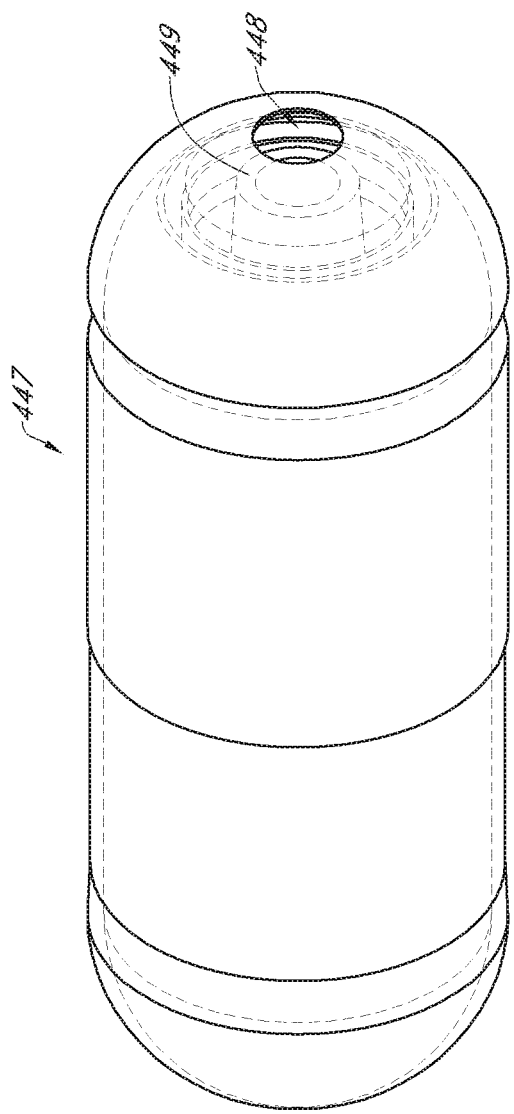

FIG. 2A depicts selected components of a swallowable, self-inflating intragastric balloon system of a preferred embodiment, including a silicone head 441 with radioopacity ring 442, trimmed 30 D silicone septum 443, Nylon 6 inoculation spacer 444, compacted balloon 445, inner container 446, and outer container 447 as constituents of the system in unassembled form. FIG. 2B depicts a fully assembled outer container 447 including vent hole 448 aligned with septum 449 for puncture to inject liquid activation agent. As discussed further below, the components of particularly preferred systems possess the attributes described herein; however, in certain embodiments systems can be employed which utilize components having other attributes and/or values.

Balloon

The balloon is fully sealed 360 degrees around with no external opening or orifice to the central lumen. The balloon has an "inverted" configuration. The term "inverted" as used herein is a broad term, and is to be given its ordinary and customary meaning to a person of ordinary skill in the art (and is not to be limited to a special or customized meaning), and refers without limitation to a balloon having a smooth external surface with seams, welds, or the inside the balloon. In order to create a balloon with an inverted configuration, e.g., a balloon with no external seam allowance (no wall material between the edge of the balloon and the weld, seam, or other feature joining the sides together), two balloon halves are joined together in some fashion (e.g., adhered using adhesive or heat or the like based on the balloon material used). One of the balloon halves encompasses an opening to allow for the balloon to be pulled through itself after adherence of the two halves and to have the seams of the balloon on the inside. The opening created is preferably circular but can be any similar shape, and the diameter of the opening preferably does not exceed 3.8 cm; however, in certain embodiments a larger diameter may be acceptable. A patch of material is adhered (adhesively, heat welded, or the like, based on the material used) to cover the original balloon-half opening. The inversion hole thus created that is subsequently patched is small enough that the forces exerted during inflation do not compromise the material used to maintain $CO_2$ gas in the balloon. The preferred shape for the inflated balloon in final assembly is ellipsoid, preferably spheroid or oblate spheroid, with nominal radii of from 1 inch (2.5 cm) to 3 inches (7.6 cm), a nominal height of from 0.25 inches (0.6 cm) to 3 inches (7.6 cm), a volume of from 90 cm$^3$ to 350 cm$^3$ (at 37° C. and at internal nominal pressure and/or full inflation), an internal nominal pressure (at 37° C.) of 0 psi (0 Pa) to 15 psi (103421 Pa), and a weight of less than 15 g. The balloon is configured for self-inflation with $CO_2$ and is configured to retain more than 75% of the original nominal volume for at least 25 days, preferably for at least 90 days when residing in the stomach.

A self-sealing valve system is attached to the balloon (e.g., on its inside surface) without the use of an opening, orifice, or other conduit in the wall of the balloon. The valve system utilizes a septum with a durometer of 20 Shore A to 60 Shore D. The valve is inserted or otherwise fabricated into a retaining structure that has a higher durometer, e.g., 40 Shore D to 70 Shore D or more. The retaining structure is fabricated from a silicone, rubber, soft plastic or any suitable non-metallic polymeric material such as an acrylic, an epoxy, a thermoplastic elastomer, or thermoplastic polyurethane. Preferably, a structure, such as a ring, that is metallic or non-metallic but radioopaque (e.g., barium) and visible under X-ray, is embedded in the retaining structure. Using a mechanical fit mechanism of two structures of different durometers, one softer (septum) with a large diameter, is inserted into a snug, more rigid durometer structure creates compressive forces in the once open orifice to enable $CO_2$ retention and reduce susceptibility for $CO_2$ gas leaks. The metallic ring for radio-opacity also helps to create compressive forces on the septum. The self-sealing septum allows air to be evacuated from the balloon for processing/compacting and inserting in the outer container, and also allows for the inflation agent to be injected into the outer container for inflation initiation. Additional septums can be provided, if desired; however, it is generally preferred to employ a single septum so as to maintain the volume of the deflated/folded balloon (and thus the outer capsule) as small as possible. The valve system is preferably attached to the inner surface of the balloon such that a shear force greater than 9 lbs (40 N) is required to dislodge the valve system. The septum can be wedge-shaped.

Inner Container

The inner container is contained within the lumen of the balloon and contains the $CO_2$ generator for balloon self-inflation. The $CO_2$ generator comprises an inflation agent mixture housed within the container. Preferably, from about 10% to about 80% of the total inflation agent used comprises powdered citric acid, with the remainder comprising powdered sodium bicarbonate. Sufficient inflation agent is provided such that upon completion of the $CO_2$ generating reaction, the balloon achieves inflation at the nominal inflation pressure described above. Preferably, a total of from about 0.28 to 4 grams inflation agent mixture is employed, depending upon the balloon size to be inflated; preferably up to 1.15 grams of sodium bicarbonate is used with the remainder being powdered citric acid to generate 300 cm$^3$ of $CO_2$ at nominal pressure.

The inflation agent is compressed, formed or otherwise held in a shape which provides good surface area availability for the reactants for $CO_2$ generation, while minimizing the space and/or volume sufficient to hold the inner container. Preferably, the inner container has a length (longest dimension) of from about 0.748 inches (1.9 cm) to 1.06 inches (2.7 cm) and a diameter or width of from about 0.239 inches (0.6 cm) to about 0.376 inches (1 cm). The volume of the inner container is preferably from about 0.41 ml to about 1.37 ml. The inner container is preferably in the form of a standard gelatin capsule but a gelatin tape may be used in lieu of a push fit capsule. The container is preferably relied upon for containing the inflation agent; however, additional sealing or other encapsulation can be employed to control timing of inflation. Gelatin is particularly preferred for use as the inner container; however other materials can also be suitable for use, e.g., cellulose. In order to minimize the internal volume of the system, it is generally preferred to include only a single inner container; however, in certain embodiments two or more internal containers can advantageously be employed. Timing of self-inflation is selected based on a normal esophageal transit time and a normal time of gastric emptying of large food particles, such that the balloon does not inflate to a size that would block the esophageal passageway or prematurely pass through the pyloric sphincter. Timing is also derived by compacting the balloon such that the activation agent is substantially localized in the balloon next to the inner capsule, creating an efficient $CO_2$ self-inflation method. I was able to get through the body this evening and attached are a few edits (very minor). Balloon inflation is initiated by the liquid activation agent causing degradation of the inner container, such that the inflation agent in the inner container contacts the liquid activation agent, thereby initiating the gas generation reaction.

An inoculation spacer is preferably incorporated to guide a needle into the self-sealing valve for injection of liquid activation agent into the lumen of the balloon and to prevent the needle from penetrating the wall of the deflated/folded balloon elsewhere such that pressure within the lumen of the balloon cannot be maintained. The inoculation spacer also facilitates preventing liquid activation agent from penetrating the inner container or the folded balloon material, thereby focusing the activation agent in an appropriate manner to properly mix the reactants for $CO_2$ generation according to the criteria described above. The inoculation spacer is generally in the form of a tube or cylinder. The inoculation spacer is preferably attached to the inner container and/or the self-sealing valve system with an adhesive or other fixing means; however, in certain embodiments the inoculation spacer can be "free-floating" and maintained in position by the folding or rolling of the walls of the balloon. The inoculation spacer can comprise any suitable material that can be passed after separation, erosion, degradation, digestion, and/or dissolution of the outer container; however, preferable materials include non-metallic materials with a minimum Shore D durometer of 40 or more, any metallic material, or a combination thereof. A cupped needle stop (inoculation spacer) can advantageously be employed.

Outer Container

The balloon is preferably provided in a deflated and folded state in a capsule or other retaining, containing or coating structure ("outer container"). The outer container is preferably in the form of a standard push-fit gelatin capsule, with the push-fit relied upon for containing the deflated/folded balloon; however, a gelatin wrap can advantageously be employed in certain embodiments. Gelatin is particularly preferred for use as the outer container; however other materials can also be suitable for use, e.g., cellulose, collagen, and the like. Preferably, the outer container has a length (longest dimension) of from about 0.95 inches (2.4 cm) to 2.5 inches (6.3 cm) and a diameter or width of from about 0.35 inches (0.9 cm) to about 0.9 inches (2.4 cm). The volume of the inner container is preferably from about 1.2 ml to about 8.25 ml. The outer container is preferably configured with one or more holes, slits, passageways or other egresses, preferably on each end, which act as vents such that any gas created due to inflation agent exposure to condensation or other ambient moisture present during processing does not cause premature separation or degradation of the inner container prior to 30 seconds after inoculation of the liquid activation agent, which may have an undesirable effect on reaction efficiency. The outer capsule degrades (e.g., separates, dissolves, or otherwise opens) due to pressure build up caused by inflation of the balloon.

Inflation

The swallowable, self-inflating intragastric balloon is provided with mechanisms to reliably control timing of self-inflation such that premature inflation while in the esophagus during swallowing is avoided and sufficient inflation once in the stomach so as to prevent passage through the pyloric sphincter is ensured. Normal esophageal transit time for large food particles has been documented as 4-8 seconds, and gastric emptying of large food particles through the pylorus does not occur for at least 15-20 minutes. The outer container is preferably configured to separate, dissolve, degrade, erode, and/or otherwise allow the deflated/folded balloon to begin unfolding not less than 60 seconds but not more than 15 minutes after inoculation with liquid activation agent. The inner container is preferably configured chemically, mechanically or a combination thereof to retard the initial $CO_2$ generating chemical reaction such that sufficient $CO_2$ to begin inflating the balloon is not available earlier than 30 seconds after inoculation with the liquid activation agent, but to permit generation of sufficient $CO_2$ such that at least 10% of the occupyable volume of the balloon is filled within 30 minutes, at least 60% of the occupyable volume of the balloon is filled within 12 hours, and at least 90% of the occupyable volume of the balloon is filled within 24 hours. This timing allows for injection of the activation agent into the outer container by the medical professional, passing the device to the patient, and swallowing by normal peristaltic means by the patient. This timing also prohibits potential passing of an uninflated balloon into the duodenum by the balloon being inflated to a sufficient size such that gastric emptying of the balloon would not be easy, as objects more than 7 mm in diameter do not readily pass.

The activation agent is preferably injected using a syringe having a needle with a gauge diameter of from 25 to 32. The needle length is preferably from about 0.25 inches (0.6 cm) to 1 inches (2.54 cm) in length so as to create a flow rate that allows for delivery of the full volume of inflation agent within 30 seconds, but in a manner/stream/flow that does not physically damage the inner container, thereby causing premature $CO_2$ generation and inflation. The activation agent is preferably pure water, or a solution containing up to 50% concentration of anhydrous citric acid at 20° C., or the equivalent thereof at varying solution temperatures based on solubility of anhydrous citric acid. Preferably, the system is configured to have an occupyable void space in the central lumen of the balloon when in compacted form in the outer container of from about 0.3 ml to about 4.5 ml, such that a corresponding volume of activation agent can be injected into the void space.

Prior to placement in the outer container of the balloon containing the inner container, the balloon is deflated and folded. In a deflated state, the balloon is flat, with the inverted seam extending around the perimeter of the balloon. The self-sealing valve system is affixed to the inner wall of the lumen close to the center of the deflated balloon, with the inner container positioned adjacent to the self-sealing valve system. The walls of the balloon are then folded. As part of the balloon design, the self-sealing valve system is manufactured in a manner such that it is placed "off center" to minimize the number of folds upon themselves (e.g., doubling or tripling up) required to fit the balloon in the outer container. For example, the self-sealing valve system can advantageously be placed ½ r±¼ r from the center of the balloon, wherein r is the radius of the balloon along a line extending from the center of the balloon through the septum.

Prior to folding, the free-floating inner container with inflation agent for $CO_2$ generation is preferably vertically aligned with the self-sealing valve system such that the septum/inoculation spacer is placed directly above the tip of the capsule. The balloon contains an inner container. A self-sealing valve system is adhesively adhered to the interior of the wall of the balloon, and the inverted configuration of the balloon is provided by inversion through a hole sealed with a patch. The top approximate ¼ of the balloon wall is folded over the inner capsule, and the pleats where the capsule is are creased similar to the pleats formed in the second step of making a paper airplane, then folded over to the left or to the right. The bottom approximate ¾ of the sphere is then accordioned using no more than 2 creases and folded over the capsule. The left half is then folded over the right half of the capsule or vice versa so that the wings touch. Then the material is rolled over until it creates a tight roll. The device is then placed in the outer container.

The balloon is folded so as to form a pocket around the inner capsule is formed to insure that the liquid injected through the self-sealing valve system is contained in an area less than 10% of the entire balloon surface area. The balloon is folded such that the number of total folds is minimized so as to minimize possible damage to the outer material or compromise of $CO_2$ barrier properties. The number of total folds is preferably less than 10 folds. The balloon material is rolled when at all possible such that the number of creases required to fit the balloon in an outer container is minimized. This is done in effort to also to prevent lumen material damage. The self-sealing valve is also preferably constructed off-center of the balloon so as to minimize the number of folds that layer on top of each other.

The material forming the wall of the balloon is processed and folded to maximize reaction efficiency by localizing the initiation agent injected into the balloon so that it is maintained proximal to the reactants within the inner container. The balloon is folded such that once the reaction initiates and the outer container separates, the balloon unfolds in a manner that creates the largest possible surface area, which prohibits the balloon from readily passing through the pyloric sphincter. The ratio of reactants in the inflation agent and activation agent are selected such that the pH of any remnant liquid inside the lumen of the balloon is acidic, with a pH of less than 6, such that any balloon leakage or breach that allows stomach acid to enter does not cause additional $CO_2$ generation and resulting unintentional re-inflation.

Deflation

The swallowable, self-inflating intragastric balloon is provided with mechanisms to reliably control timing of deflation. In preferred embodiments, the balloon auto-deflates and passes through the stomach, through the lower gastrointestinal tract, and out of the body. In the preferred embodiments described below, the timing of deflation can be accomplished via the external gastric environment (by conditions of temperature, humidity, solubility, and/or pH, for example) or via the environment within the lumen of the inflated balloon.

In other embodiments, the patch applied to allow for inverted seams as described above and/or one or more additional patches or other structures added to the balloon construction are made out of an erodible, degradable, or dissolvable material (natural or synthetic) and are incorporated into the wall of the balloon. The patch(es) are of sufficient size to ensure opening of a sufficient surface area to cause rapid deflation, and to prevent re-inflation by seepage of stomach fluid into the balloon. The balloon patch(es) comprise materials that can be applied to the balloon such that a substantially smooth surface is maintained, and preferably comprise a single layer or multi-layered material. The patch(es) are constructed using an erodible, disintegrable, degradable or other such material that is preferably tissue-compatible and degrades into non-toxic products or is a material that slowly hydrolyzes and/or dissolves over time (e.g., poly(lactic-co-glycolic acid) (PLGA), polyvinyl alcohol (PVOH), polylactic acid (PLA), poly-L-lactic acid PLAA, Pullulan, Polyethylene Glycol (PEG), polyanhydrides, polyorthoesters, polyaryletherketones (PEEK), multi-block polyetheresters, poliglecaprone, polydioxanone, polytrimethylene carbonate, and other similar materials). These erodible, disintegrable, or degradable materials can be used alone, or in combination with other materials, or can be cast into/co-extruded, laminated, and/or dip coated in conjunction with non-erodible polymers (e.g., PET or the like) and employed in the construction of the balloon. Degradation/erosion occurs, is initiated by, and/or is controlled by the gastric environment (e.g., by conditions of temperature, humidity, solubility, and/or pH, for example), or is controlled within the lumen of the balloon (e.g., by conditions of humidity and/or derived pH, for example) based on what the patch is exposed to. Thickness of the polymer as well as environment which affects degradation and time of exposure can also facilitate degradation timing. Degradation/erosion are timed such that they occur once the pre-determined balloon useful life is completed (e.g., inflation is maintained for from 25 to 90 days in vivo in the stomach before degradation/erosion results in formation of an opening permitting deflation). As an alternative to (or in connection with) using an degradable material for the patch, the patch can comprise a similar $CO_2$ barrier film or the same film as the remaining wall of the balloon which is adhered to the balloon using a weak adhesive, or welded or adhered such that after a specified amount of time the patch delaminates from the applied area and allows for an opening for $CO_2$ release for deflation. The mechanism of using an erodible material, or a material that mechanically fails after a pre-specified time is be similar for all embodiments for deflation mechanisms described below as well. The timing of degradation or erosion can be controlled using the external gastric environment (e.g., by conditions of temperature, humidity, solubility, and/or pH, for example) and/or can be controlled by conditions within the lumen of the balloon (e.g., by conditions of humidity and/or pH of residual liquid in the balloon).

In other embodiments, a plug or plugs (optionally in conjunction another degradable retaining structure) can be incorporated into the balloon construction and can consist, all or in part, of an erodible, disintegrable, or otherwise degradable synthetic or natural polymer similar to those described above (e.g., PLGA, PLAA, PEG, or the like). The plug can be formed into various shapes (e.g., cylinder shape) to achieve various surface-to-volume ratios so as to provide a preselected and predictable bulk degradation pattern for the erodible polymer. The plug can incorporate a releasing mechanism that can be chemically initiated after degradation/erosion begins, such that the septum or plug material pops out of the balloon or falls inside of the balloon, thereby creating a passageway for $CO_2$ gas release and subsequent deflation of the balloon. Mechanical additions that can be used in conjunction with a plug include a compressed spring housed within the retaining structure or plug structure, or a degradable/erodible/disintegrable material that holds a plug (e.g., of a nondegradable or degradable material) in place. Once the material degrades, the spring is released and/or the plug/septum is pulled into the balloon or pushed out of the balloon, thus releasing $CO_2$ gas once an orifice has been created by release of the spring mechanism and pushing out or pulling in of the plug.

In certain embodiments, the balloon can incorporate one or more plugs in the wall of the balloon that contain a compressed pellet or gas releasing pellet. The pellet can be comprised of any combination of constituents that, when activated, emit $CO_2$ gas (e.g., sodium bicarbonate and citric acid, or potassium bicarbonate and citric acid, or the like). The pellet can be in tablet or rod form protected by an erodible, disintegrable, or degradable material that is preferably tissue-compatible and degrades into non-toxic products or that slowly hydrolyzes and/or dissolves similarly to the plugs and patches described above (e.g., poly(lactic-co-glycolic acid) (PLGA), polyvinyl alcohol (PVOH), polylactic acid (PLA), poly-L-lactic acid PLAA, Pullulan, Polyethylene Glycol, polyanhydrides, polyorthoesters, polyaryletherketones (PEEK), multi-block polyetheresters, poliglecaprone, polydioxanone, polytrimethylene carbonate, and other like materials). Degradation/erosion of the plug initiates the reaction of the two chemicals in the pellet and subsequently leads to formation of gas (e.g., $CO_2$). As sufficient gas is trapped or built up, sufficient pressure is eventually generated to push out the softened polymer material and create a larger channel for the $CO_2$ gas in the balloon to escape. External pressure applied by the stomach to the balloon (e.g., squeezing) can contribute to the process of creating a larger channel. Dimensions and properties of the plug (diameter, thickness, composition, molecular weight, etc.) comprised of the polymer drives the timing of degradation.

In other embodiments, plugs or patches of different shapes or sizes similar to those of the plugs described above can be employed within the balloon lumen in a multi-layer configuration including a semi-permeable membrane to facilitate balloon deflation. The plug or patch is made of similar degradable/erodible/dissolvable material as described above (e.g., poly(lactic-co-glycolic acid) (PLGA), polyvinyl alcohol (PVOH), polylactic acid (PLA), PLAA, pullulan, and other like materials) and contains a compartment enclosed by a semi-permeable membrane (impermeable to an osmolyte) that contains a concentrated solution of a solute or osmolyte (such as glucose, sucrose, other sugars, salts, or combination thereof). Once the plug or patch begins to degrade or erode, the water molecules move by osmosis down the water gradient from the region of greater water concentration to the region of lower water concentration across the semi-permeable membrane into the hypertonic solution in the compartment. The compartment containing the osmolyte swells and eventually bursts, pushing the membranes and the degraded plug or patch out, thereby allowing rapid gas loss through the newly created channels or areas.

Another mechanism for self-deflation is to create a forced de-lamination scheme, which can provide a larger surface area to ensure rapid deflation. In, e.g., a balloon having a tri-layer wall, the outermost layer is substantially strong enough to hold $CO_2$ (e.g., polyethylene terephthalate (PET) or the like), the middle layer is comprised entirely of an erodible material (e.g., PVOH or the like) while the inner layer is comprised of a weaker material (e.g., polyethylene (PE) or the like). The PET or outermost layer is "scored" or hatched with erodible material to create small channels that erode over time. This creates channels such that the gastric fluid seeps into the balloon layers and starts degrading the fully erodible material. When the erodible layer degrades or dissolves, the material that composes the innermost layer also erodes, degrades or dissolves since it is not strong enough to withstand the gastric forces/environment on its own. The balloon then collapses on itself and eventually passes through the lower gastrointestinal tract. Having an erodible layer sandwiched between a strong and weak layer facilitates timing of erosion by creating a longer path length than an erodible plug or patch affected by the gastric environment. The distance between scores or openings can also be selected so as to provide a desired deflation rate.

A mechanism to facilitate passing involves an erosion mechanism that allows for the balloon to be broken down into a size that has a higher probability of predictably passing through the lower gastrointestinal system. Preferably, the size of the balloon as deflated is less than 5 cm long and 2 cm thick (similar to various foreign objects of similar size that have been shown to pass predictably and easily through the pyloric sphincter). This can be accomplished by providing the balloon with "erodible seams". One seam that breaks the balloon open into (at a minimum) two halves, or more seams are provided so that a plurality of smaller balloon pieces is produced in the dissociation reaction. The number of seams used can be selected based on the original surface area of the balloon and what is required to dissociate the balloon into pieces that are of a size that can predictably pass through the gastrointestinal tract more easily. The rate of seam erosion can be controlled by using a material affected by, e.g., the external gastric environment pH, liquid, humidity, temperature, or a combination thereof. Seams can be single layer consisting of only erodible material, or multi-layer. The timing of self-deflation can be further controlled by the design of the seam layers, e.g., making the reaction and/or degradation of the seam material dependent on the internal environment of the balloon instead of the external environment. By manipulating the reaction such that erosion or degradation is initiated by the internal environment (e.g., the balloon's internal pH, humidity, or other factors), any impact of person-to-person gastric variability (pH, etc.) that could affect erosion timing is minimized. The internal balloon environment can be manipulated by adding excess water at injection to create a more humid internal environment, or the amount of constituents added can be varied to manipulate the pH, etc.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

All references cited herein are incorporated herein by reference in their entirety. To the extent publications and patents or patent applications incorporated by reference contradict the disclosure contained in the specification, the specification is intended to supersede and/or take precedence over any such contradictory material.

To the extent publications and patents or patent applications incorporated by reference herein contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, unless otherwise expressly stated, should be construed as open ended as opposed to limiting. As examples of the foregoing, the term 'including' should be read to mean 'including, without limitation' or the like; the term 'comprising' as used herein is synonymous with 'including,' 'containing,' or 'characterized by,' and is inclusive or open-ended and does not exclude additional, unrecited elements or method steps; the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise. In addition, as used in this application, the articles 'a' and 'an' should be construed as referring to one or more than one (i.e., to at least one) of the grammatical objects of the article. By way of example, 'an element' means one element or more than one element.

The presence in some instances of broadening words and phrases such as 'one or more', 'at least', 'but not limited to', or other like phrases shall not be read to mean that the narrower case is intended or required in instances where such broadening phrases may be absent.

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. An intragastric balloon system comprising a composite wall structure configured to maintain a $CO_2$ leak rate of less than or equal to 40 $cc/m^2/day$ at 37° C., wherein the composite wall structure comprises:
    a supporting film structure having a Young's Modulus of 500 Mpa or greater;
    a first $CO_2$ barrier layer configured such that its $CO_2$ barrier properties are not substantially affected by exposure to humidity levels within the gastric environment or within a central lumen of the balloon system; and
    a second $CO_2$ barrier layer configured such that its $CO_2$ barrier properties are not substantially affected by mechanical forces during processing, compacting, or application of external gastric pressures;
    wherein the first $CO_2$ barrier layer comprises a silicon dioxide layer having a thickness of from about 100 Å to about 800 Å and the second $CO_2$ barrier layer comprises an ethylene vinyl alcohol layer having a thickness of at least about 2 microns.

2. The intragastric balloon system of claim 1, wherein the supporting film structure comprises a polyethylene terephthalate layer.

3. The intragastric balloon system of claim 2, wherein the silicon dioxide layer is provided as a coating on one side of the polyethylene terephthalate layer.

4. The intragastric balloon system of claim 3, wherein the ethylene vinyl alcohol layer is situated between two polyethylene layers, wherein the ethylene vinyl alcohol layer and the two polyethylene layers are bonded together with tie layers, and wherein the silicon dioxide layer is adhesively bonded to one of the polyethylene layers.

5. The intragastric balloon system of claim 1, wherein the ethylene vinyl alcohol layer is extruded.

6. The intragastric balloon system of claim 5, wherein the ethylene vinyl alcohol layer is co-extruded with one or more layers of polyethylene.

7. The intragastric balloon system of claim 5, wherein the ethylene vinyl alcohol layer is sandwiched between two polyethylene layers.

8. The intragastric balloon system of claim 1, wherein the intragastric balloon system is configured to be swallowable.

9. The intragastric balloon system of claim 1, wherein the intragastric balloon system is configured to be swallowable and self-inflating.

10. The intragastric balloon system of claim 9, further comprising a self-sealing valve system attached to the composite wall structure of the balloon system in the central lumen of the balloon system by an adhesive with a shear force greater than about 40 N, the self-sealing valve system comprising a septum, a retaining structure, and a continuous ring, wherein the septum has a durometer that is less than a durometer of the retaining structure, wherein the continuous ring is configured to exert a compressive force on the septum, wherein the balloon system has a weight of less than about 15 g, wherein the balloon system is configured to have a shape upon full inflation selected from the group consisting of ellipsoid, spheroid, and oblate spheroid, and wherein the balloon system is configured to have a volume of from about 90 $cm^3$ to about 350 $cm^3$ upon full inflation.

11. The intragastric balloon system of claim 10, further comprising an inner container within the central lumen of the balloon system, the inner container containing from about 0.28 grams to about 4 grams of an inflation agent, wherein up to about 80 wt. % of a total amount of the inflation agent is powdered citric acid, with a remainder of the inflation agent comprising powdered sodium bicarbonate.

* * * * *